(12) United States Patent
Ozawa et al.

(10) Patent No.: US 12,226,497 B2
(45) Date of Patent: Feb. 18, 2025

(54) METHOD FOR PRODUCING COATING FILM

(71) Applicant: KAO CORPORATION, Tokyo (JP)

(72) Inventors: Satoshi Ozawa, Adachi-ku (JP); Yu Saito, Shinagawa-ku (JP); Akio Kashimoto, Funabashi (JP)

(73) Assignee: KAO CORPORATION, Tokyo (JP)

( * ) Notice: Subject to any disclaimer, the term of this patent is extended or adjusted under 35 U.S.C. 154(b) by 1048 days.

(21) Appl. No.: 17/266,880

(22) PCT Filed: Aug. 8, 2019

(86) PCT No.: PCT/JP2019/031285
§ 371 (c)(1),
(2) Date: Feb. 8, 2021

(87) PCT Pub. No.: WO2020/032151
PCT Pub. Date: Feb. 13, 2020

(65) Prior Publication Data
US 2021/0299005 A1 Sep. 30, 2021

(30) Foreign Application Priority Data
Aug. 9, 2018 (JP) .................................. 2018-150914

(51) Int. Cl.
*A61K 8/02* (2006.01)
*A45D 34/04* (2006.01)
(Continued)

(52) U.S. Cl.
CPC .............. *A61K 8/046* (2013.01); *A45D 34/04* (2013.01); *A61K 8/8129* (2013.01);
(Continued)

(58) Field of Classification Search
None
See application file for complete search history.

(56) References Cited

U.S. PATENT DOCUMENTS 6,514,504 B1 2/2003 Yen et al.
6,531,142 B1 3/2003 Rabe et al.
(Continued)

FOREIGN PATENT DOCUMENTS

AU  2016340485 A1  5/2018
CN  104136001 A  11/2014
(Continued)

OTHER PUBLICATIONS

Extended European Search Report issued on Apr. 19, 2022, in corresponding European Patent Application No. 19848183.0, 13 pages.

(Continued)

*Primary Examiner* — Brian Gulledge
(74) *Attorney, Agent, or Firm* — Oblon, McClelland, Maier & Neustadt, L.L.P.

(57) ABSTRACT

Provided is a method for producing a coating film formed on the skin by electrostatic spraying, the coating film having good feeling and not causing damage on the coating film even after a lapse of a long time A method for producing a coating film on the skin, comprising the steps of:
  A) electrostatically spraying a composition X comprising a component (a) and a component (b) directly onto the skin to form a coating film on a surface of the skin:
    (a) one or more volatile substances selected from the group consisting of water, an alcohol and a ketone;
    (b) a polymer capable of forming a coating film; and
  B) applying a composition Y other than the composition X, comprising a component (c) and a component (d) to the skin
in the order presented or in reverse order:
  (c) 0.5% by mass or more and less than 5% by mass of an adhesive polymer;

(Continued)

(d) one or more selected from the group consisting of a polyol and a liquid oil.

7 Claims, 1 Drawing Sheet

(51) Int. Cl.
    *A61K 8/04*     (2006.01)
    *A61K 8/34*     (2006.01)
    *A61K 8/35*     (2006.01)
    *A61K 8/81*     (2006.01)
    *A61K 8/891*     (2006.01)
    *A61K 8/898*     (2006.01)
    *A61Q 1/00*     (2006.01)
    *A61Q 1/02*     (2006.01)
    *A61Q 19/00*     (2006.01)
    *B05B 5/025*     (2006.01)

(52) U.S. Cl.
    CPC .......... *A61K 8/8152* (2013.01); *A61K 8/8176* (2013.01); *A61Q 1/00* (2013.01); *B05B 5/025* (2013.01); *A61K 2800/54* (2013.01); *A61K 2800/87* (2013.01)

(56) References Cited

U.S. PATENT DOCUMENTS

| | | | | |
|---|---|---|---|---|
| 11,497,290 | B2 * | 11/2022 | Amari | A61K 8/81 |
| 2004/0009198 | A1 * | 1/2004 | Bernard | A61K 8/25 |
| | | | | 424/401 |
| 2007/0140991 | A1 * | 6/2007 | Maitra | A61K 8/8152 |
| | | | | 424/59 |
| 2007/0259029 | A1 | 11/2007 | McEntire et al. | |
| 2014/0328776 | A1 | 11/2014 | Dong | |
| 2019/0053602 | A1 * | 2/2019 | Amari | A61K 8/35 |
| 2019/0059551 | A1 | 2/2019 | Amari et al. | |
| 2019/0343731 | A1 | 11/2019 | Amari et al. | |
| 2019/0350825 | A1 | 11/2019 | Uchiyama et al. | |
| 2020/0046618 | A1 | 2/2020 | Imai et al. | |

FOREIGN PATENT DOCUMENTS

| | | | | |
|---|---|---|---|---|
| EP | 1 348 426 | A1 | 10/2003 | |
| EP | 2 821 059 | A1 | 1/2015 | |
| JP | 10-95705 | A | 4/1998 | |
| JP | 2003-506470 | A | 2/2003 | |
| JP | 2003-507165 | A | 2/2003 | |
| JP | 2006-104211 | A | 4/2006 | |
| JP | 2009-536647 | A | 10/2009 | |
| JP | 2017-78062 | A | 4/2017 | |
| JP | 2017-78063 | A | 4/2017 | |
| JP | 2018-87186 | A | 6/2018 | |
| JP | 2018-108991 | A | 7/2018 | |
| JP | 2018-177798 | A | 11/2018 | |
| JP | 2020-63212 | A | 4/2020 | |
| TW | 201729785 | A | 9/2017 | |
| TW | 201822752 | A | 7/2018 | |
| WO | WO 00/08249 | A1 | 2/2000 | |
| WO | WO 01/12137 | A1 | 2/2001 | |
| WO | WO 01/12335 | A1 | 2/2001 | |
| WO | WO 2007/058380 | A1 | 5/2007 | |
| WO | WO-2017069079 | A1 * | 4/2017 | ............. A45D 34/04 |

OTHER PUBLICATIONS

Database GNPD[Online]MITEL; Aug. 18, 2015, anonymous: "Makeup Setting Spray", XP055578800, Database accession No. 3377203.
Database GNPD[Online]MITEL; Jan. 26, 2016, anonymous: "Super Sealer Mattifying Setting Spray", XP055904532, Database accession No. 3745895.
International Search Report issued Nov. 5, 2019 in PCT/JP2019/031285 filed Aug. 8, 2019, 2 pages.

* cited by examiner

METHOD FOR PRODUCING COATING FILM

FIELD OF THE INVENTION

The present invention relates to a method for producing a coating film.

BACKGROUND OF THE INVENTION

A method of forming a coating on the skin by electrostatic spraying has been reported. For example, Patent Literature 1 discloses a method for treating skin, the method including electrostatically spraying onto the skin with a composition. The composition used in this method contains a liquid-insulating material, a conductive material, a particulate powder material, and a thickener. Typically, a cosmetic product containing a pigment or a skincare composition is used as the composition. Specifically, a cosmetic foundation is used as the composition. That is, the inventions disclosed in Patent Literature 1 are primarily envisioned for cosmetic purposes by electrostatically spraying a cosmetic foundation to cosmetically decorate the skin. Described in Patent Literature 2 is a disposable cartridge for use in an electrostatic spraying apparatus for cosmetics.

However, it has been found that when an electrostatic spraying is performed in accordance with the methods described in Patent Literatures 1 and 2 to form a coating film on the skin, the adhesion between the skin and the coating film formed by the electrostatic spraying is not sufficient, and the coating film may be damaged or peeled off due to an external force such as friction. Therefore, the applicant found that application of a liquid agent containing water, polyols or a liquid oil at 20° C. onto the skin before or after the formation of the coating film by electrostatic spraying improves the adhesion of the coating film obtained by the electrostatic spraying, and filed a patent application therefor (Patent Literature 3).

[Patent Literature 1] JP 2006-104211-A
[Patent Literature 2] JP 2003-507165-A
[Patent Literature 3] JP 2017-78062-A

SUMMARY OF THE INVENTION

The present invention provides a method for producing a coating film on the skin, comprising the steps of:
A) directly electrostatically spraying a composition X containing a component (a) and a component (b) onto the skin to form a coating film on a surface of the skin:
  (a) one or more volatile substances selected from the group consisting of water, an alcohol and a ketone,
  (b) a polymer capable of forming a coating film; and
B) applying a composition Y other than the composition X comprising a component (c) and a component (d) to the skin
in the order presented or in the reverse order:
  (c) 0.5% by mass or more and less than 5% by mass of an adhesive polymer;
  (d) one or more selected from the group consisting of a polyol and a liquid oil.

In addition, the present invention provides a composition Y used for producing a coating film on the skin by applying it to the skin by a means other than the electrostatic spraying before or after the formation of the coating film on the skin surface by electrostatic spraying directly onto the skin, the composition Y comprising a component (c) and a component (d)

(c) 0.5% by mass or more and less than 5% by mass of an adhesive polymer;
  (d) one or more selected from the group consisting of a polyol and a liquid oil.

BRIEF DESCRIPTION OF THE INVENTION

DETAILED DESCRIPTION OF EMBODIMENT

Figure 1:
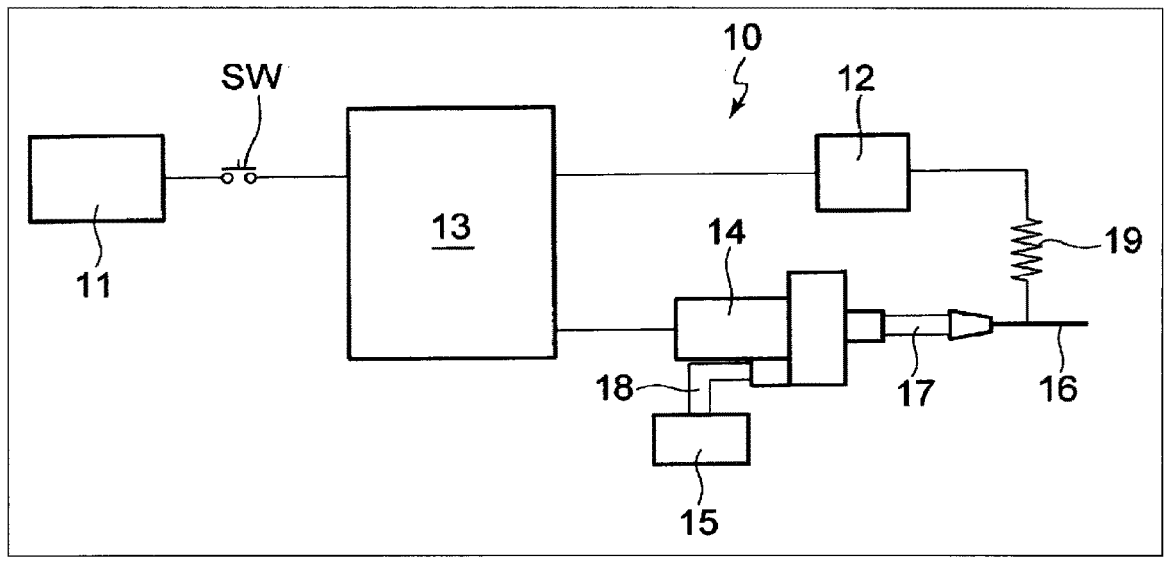
FIG. 1 is a schematic diagram showing a configuration of an electrostatic spraying apparatus suitably used in the present invention.

It was found that the coating film on the skin obtained by the method recited in Patent Literature 3 may cause an uncomfortable feeling immediately after the formation of the coating film, and that the coating may be peeled off or broken after a lapse of a long time.

Accordingly, the present invention aims to provide a method for producing a coating film formed on the skin by electrostatic spraying, the coating film imparting good feeling and not causing damage even after a lapse of a long time.

The present inventors investigated various constitutions of compositions to be applied before or after electrostatic spraying onto the skin, and found that, when a composition containing a small amount of an adhesive polymer and a polyol or a liquid oil, which is different from the composition used for electrostatic spraying, is used, a coating film can be formed which does not cause an uncomfortable feeling in a coating film immediately after the formation and hardly causes coming off or crack even after a lapse of a long time, thereby completing the present invention.

The method for producing a coating film formed on the skin by electrostatic spraying of the present invention imparts an excellent feeling, adhesion and durability because of no crack or coming off even after a lapse of a long time.

The present invention includes A) a step of directly electrostatically spraying the composition X onto the skin to form a coating film on the skin surface (step A), and B) a step of applying the composition Y onto the skin (step B). As the method for forming a coating film in the step A, the present invention employs an electrostatic spraying method. The electrostatic spraying method is a method in which a positive or negative high voltage is applied to a composition to charge the composition, and the charged composition is sprayed toward a target. The sprayed composition spreads into the space while repeatedly refining by a Coulombic repulsion, and in the process or after adhering to the target, the solvent which is a volatile substance dries, thereby forming a coating film on the surface of the target.

The above-mentioned composition X used in the present invention (hereinafter also referred to as "spraying composition") is a liquid in an environment in which an electrostatic spraying method is performed. This composition X contains the following components (a) and component (b):
  (a) one or more volatile substances selected from the group consisting of water, alcohols and ketones.
  (b) a polymer capable of forming a coating film.

Hereinafter, each component will be described.

The volatile substance as the component (a) is volatile in the state of liquid. The component (a) is compounded in the composition for spraying for the purpose of forming a coating film on the skin; the composition for spraying placed in an electric field is thoroughly charged and then discharged to the skin from the tip of a nozzle, and as the component (a) evaporates, the charge density of the composition for spraying becomes excessively high, and while particles of the composition are made even smaller due to the Coulomb repulsion, the component (a) further evaporates and consequently a dry coating film is formed on the skin. To this end, the volatile substance has a vapor pressure at 20° C. of preferably 0.01 kPa or more and 106.66 kPa or less, more preferably 0.13 kPa or more and 66.66 kPa or less, further preferably 0.67 kPa or more and 40.00 kPa or less, and still more preferably 1.33 kPa or more and 40.00 kPa or less.

A monovalent linear aliphatic alcohol, a monovalent cycloaliphatic alcohol and a monovalent aromatic alcohol, for example, are preferably used as alcohol of the volatile substances as the component (a). Examples of the monovalent linear aliphatic alcohol include alcohols having 1 to 6 carbon atoms, examples of the monovalent cycloaliphatic alcohol include cyclic alcohols having 4 to 6 carbon atoms and examples of the monovalent aromatic alcohol include benzyl alcohol and phenylethyl alcohol. Specific examples thereof include ethanol, isopropyl alcohol, butyl alcohol, phenylethyl alcohol, n-propanol and n-pentanol. One or more selected from the group consisting of these alcohols may be used.

Examples of ketones of the volatile substances as the component (a) include a dialkylketone having 1 to 4 carbon atoms such as acetone, methyl ethyl ketone and methyl isobutyl ketone. These ketones may be used singly or in combinations of two or more.

The volatile substance as the component (a) is more preferably one or more selected from the group consisting of ethanol, isopropyl alcohol, butyl alcohol and water, further preferably one or more selected from the group consisting of ethanol and butyl alcohol, and still more preferably a volatile substance containing at least ethanol.

The content of the component (a) in the composition for spraying is preferably 30% by mass or more, more preferably 55% by mass or more, and further preferably 60% by mass or more. The content is preferably 98% by mass or less, more preferably 96% by mass or less, and further preferably 94° by mass or less. The content of the component (a) in the composition for spraying is preferably 30% by mass or more and 98% by mass or less, more preferably 55% by mass or more and 96% by mass or less, and further preferably 60% by mass or more and 94% by mass or less. When the composition for spraying contains the component (a) in this ratio, the composition for spraying can thoroughly evaporate when an electrostatic spraying method is performed.

The content of ethanol is preferably 50% by mass or more, more preferably 65% by mass or more, further preferably 80% by mass or more based on the total amount of the volatile substance as the component (a). The content is preferably 100% by mass or less. The content of ethanol is preferably 50% by mass or more and 100% by mass or less, more preferably 65% by mass or more and 100% by mass or less, and further preferably 80% by mass or more and 100% by mass or less based on the total amount of the volatile substance as the component (a).

From the viewpoint of fiber formability and conductivity, the content of water is preferably less than 50% by mass, more preferably 45% by mass or less, further preferably 10% by mass or less, and still more preferably 5% by mass or less, and preferably 0.2% by mass or more, and more preferably 0.4% by mass or more based on the total amount of the volatile substance as the component (a).

The polymer capable of forming a coating film as the component (b) is usually soluble in the volatile substance as the component (a). Here, being soluble means that the polymer is in the form of dispersion at 20° C. and the dispersion is homogeneous, and preferably transparent or semi-transparent when visually observed.

A suitable polymer may be used as the polymer capable of forming a coating film depending on the properties of the volatile substance as the component (a). More specifically, the polymer capable of forming a coating film is roughly classified into water-soluble polymers and water-insoluble polymers. In the present description, the "water-soluble polymer" refers to a polymer with such a characteristic that when 1 g of the polymer is weighed in an environment of 1 atm and 23° C. and then immersed in 10 g of ion exchange water for 24 hours, 0.5 g or more of the polymer which has been immersed dissolves in water. Meanwhile, the "water-insoluble polymer" in the present description refers to a polymer with such a characteristic that when 1 g of the polymer is weighed in an environment of 1 atm and 23° C. and then immersed in 10 g of ion exchange water for 24 hours, 0.5 g or more of the polymer which has been immersed does not dissolve in water.

Examples of water-soluble polymers capable of forming a coating film include mucopolysaccharides such as pullulan, hyaluronic acid, chondroitin sulfate, poly-γ-glutamic acid, modified corn starch, β-glucan, glucooligosaccharide, heparin and keratosulfate, natural polymers such as cellulose, pectin, xylan, lignin, glucomannan, galacturonic acid, psyllium seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose and hydroxypropyl methyl cellulose; and synthetic polymers such as partially saponified polyvinyl alcohol (when not used in combination with a cross-linking agent), low-saponified polyvinyl alcohol, polyvinyl pyrrolidone (PVP), polyethylene oxide and sodium polyacrylate. These water-soluble polymers may be used singly or in combinations of two or more. Of these water-soluble polymers, pullulan and synthetic polymers such as partially saponified polyvinyl alcohol, low-saponified polyvinyl alcohol, polyvinyl pyrrolidone and polyethylene oxide are preferably used because a coating film is easily produced. When polyethylene oxide is used as the water-soluble polymer, polyethylene oxide has a number average molecular weight of preferably 50,000 or more and 3,000,000 or less, and more preferably 100,000 or more and 2,500,000 or less.

Meanwhile, examples of water-insoluble polymers capable of forming a coating film include completely saponified polyvinyl alcohol, which can be insolubilized after forming a coating film, partially saponified polyvinyl alcohol, which can be cross-linked after forming a coating film when used in combination with a cross-linking agent, an oxazoline-modified silicone such as a poly(N-propanoylethyleneimine)-grafted dimethylsiloxane/γ-aminopropylmethylsiloxane copolymer, polyvinylacetal diethylaminoacetate, Zein (main component of corn protein), polyester, polylactic acid (PLA), an acrylic resin such as polyacrylonitrile resin and polymethacrylic acid resin, polystyrene resin, polyvinyl butyral resin, polyethylene terephthalate resin, polybutylene terephthalate resin, polyurethane resin, polyamide resin, polyimide resin and polyamideimide resin. These water-insoluble polymers may be used singly or in combinations of two or more. Of these water-insoluble polymers, one or more selected from the group consisting of completely saponified polyvinyl alcohol, which can be insolubilized after forming a coating film, partially saponified polyvinyl alcohol, which can be cross-linked after forming a coating film when used in combination with a cross-linking agent, polyvinyl butyral resin, polyurethane resin, an oxazoline-modified silicone such as a poly(N-propanoylethylene-imine)-grafted dimethylsiloxane/γ-aminopropylmethylsiloxane copolymer, polyvinylacetal diethylaminoacetate and Zein are preferably used. One or more selected from the group consisting of polyvinyl butyral resin and polyurethane resin are more preferably used.

The content of the component (b) in the composition for spraying is preferably 2% by mass or more, more preferably 4% by mass or more, and further preferably 6% by mass or more. The content is 50% by mass or less, more preferably 45% by mass or less, and further preferably 40% by mass or less. The content of the component (b) in the composition for spraying is preferably 2% by mass or more and 50% by mass or less, more preferably 4% by mass or more and 45% by mass or less, and further preferably 6% by mass or more and 40% by mass or less. When the composition for spraying contains the component (b) in this ratio, a coating film which is made of a deposit of fiber, covers the surface of the bear skin and has excellent durability over time with little smudging can be successfully formed.

The ratio of the content of the component (a) to the component (b) in the composition for spraying, (a)/(b), is preferably 0.5 or more and 40 or less, more preferably 1 or more and 30 or less, and further preferably 2 or more and 25 or less because the component (a) can be thoroughly evaporated when performing an electrostatic spraying method.

Furthermore, the ratio of the content of ethanol to the component (b) in the composition for spraying, (a)/(b), is preferably 0.5 or more and 40 or less, more preferably 1 or more and 30 or less, and further preferably 2 or more and 25 or less because the component (a) can thoroughly evaporate when performing an electrostatic spraying method.

The composition for spraying may also contain a glycol. Examples of the glycol include ethylene glycol, propylene glycol, butylene glycol, diethylene glycol, dipropylene glycol and polypropylene glycol. The content of the glycol is preferably 10% by mass or less, more preferably 3% by mass or less, and further preferably 1° by mass or less in the composition for spraying because the component (a) can thoroughly evaporate when performing an electrostatic spraying method. It is preferable that the composition for spraying contain substantially no glycol.

The composition for spraying may also contain a powder. Examples of the powder include a color pigment, an extender, a pearl pigment and an organic powder. The content of the powder is preferably 5% by mass or less, more preferably 3% by mass or less, and further preferably 1% by mass or less in the composition for spraying in order to give smooth feeling on the surface of the skin. It is preferable that the composition for spraying contain substantially no powder.

The composition for spraying may contain only the component (a) and the component (b) described above, or other components in addition to the component (a) and the component (b). Examples of other components include an oil agent such as di(phytosteryl/octyl dodecyl) lauroyl glutamate, a surfactant, an UV protection agent, a flavoring agent, a repellent, an antioxidant, a stabilizer, an antiseptic, an antiperspirant and vitamins. These agents may be used for not only the original purpose but also other purposes depending on the purpose of use. For example, an antiperspirant may be used as a flavoring agent. Alternatively, in combination with a different purpose, an agent having, for example, the effect of an antiperspirant and the effect of a flavoring agent may be used. When the composition for spraying contains other components, the ratio of the content of these other components is preferably 0.1% by mass or more and 30% by mass or less, and more preferably 0.5% by mass or more and 20% by mass or less.

In the method of the present invention, the composition for spraying is electrostatically sprayed to the skin directly before or after the Step B to form a coating film on the surface of the skin.

When an electrostatic spraying method is performed, a composition for spraying having a viscosity at 25° C. of preferably 1 mPa·s or more, more preferably 10 mPa·s or more, and further preferably 50 mPa·s or more is used. Furthermore, a composition for spraying having a viscosity at 25° C. of preferably 5,000 mPa·s or less, more preferably 2,000 mPa·s or less, and further preferably 1,500 mPa·s or less is used. The composition for spraying has a viscosity at 25° C. of preferably 1 mPa·s or more and 5,000 mPa·s or less, more preferably 10 mPa·s or more and 2,000 mPa·s or less, and further preferably 50 mPa·s or more and 1,500 mPa·s or less. Using a composition for spraying having a viscosity in that range makes it possible to form a coating film, in particular a porous coating film made of a deposit of fiber, successfully by an electrostatic spraying method. Formation of a porous coating film is advantageous in that sweaty skin and the like is further prevented, coating film becomes more adhesive to the skin, and the coating film can be removed from the skin easily and completely. The viscosity of the composition for spraying is measured by an E-type viscometer at 25° C. An E-type viscometer made by TOKYO KEIKI INC., for example, may be used as the E-type viscometer. Rotor No. 43 may be used as a rotor in that case.

The composition for spraying may be directly sprayed to the human skin by an electrostatic spraying method. The electrostatic spraying method includes an electrostatic spraying step in which the composition for spraying is electrostatically sprayed to the skin using an electrostatic spraying apparatus to form a coating film. The electrostatic spraying apparatus has a container for storing the composition for spraying, a nozzle for discharging the composition for spraying, a unit for supplying the composition for spraying stored in the container to the nozzle, and a power source for applying voltage to the nozzle. FIG. 1 is a schematic diagram showing the structure of an electrostatic spraying apparatus preferably used in the present invention. The electrostatic spraying apparatus 10 shown in FIG. 1 has a low-voltage power source 11. The low-voltage power source 11 can generate a voltage of several volts to dozens of volts. It is preferable that the low-voltage power source 11 consist of one or more batteries in order to increase portability of the electrostatic spraying apparatus 10. Furthermore, using a battery for the low-voltage power source 11 is advantageous in that the battery can be easily replaced according to need. AC adapters and the like may also be used as the low-voltage power source 11 instead of batteries.

The electrostatic spraying apparatus 10 also has a high-voltage power source 12. The high voltage power source 12 is connected to the low-voltage power source 11 and has an electronic circuit (not shown) which increases the voltage generated in the low-voltage power source 11 to high voltage. The electronic circuit for increasing voltage usually consists of a transformer, a capacitor, a semiconductor element and the like.

The electrostatic spraying apparatus 10 also has an auxiliary electronic circuit 13. The auxiliary electronic circuit 13, which is interposed between the low-voltage power source 11 and the high-voltage power source 12 described above, has the function of adjusting the voltage in the low-voltage power source 11 to operate the high-voltage power source 12 in a stable manner. The auxiliary electronic circuit 13 also has the function of controlling the rotation number of a motor provided in a pump mechanism 14 described later. By controlling the rotation number of the motor, the amount of the composition for spraying to be supplied to the pump mechanism 14 from a container 15 for the composition for spraying described later is controlled. A switch SW is installed between the auxiliary electronic circuit 13 and the low-voltage power source 11, and the electrostatic spraying apparatus 10 is operated/stopped by turning on/off the switch SW.

The electrostatic spraying apparatus 10 also has a nozzle 16. The nozzle 16 is made of a conductive material such as metal or a non-conductive material such as plastic, rubber and ceramic, and has a shape that can discharge the composition for spraying from the tip. In the nozzle 16, a small space through which the composition for spraying passes is formed in the longitudinal direction of the nozzle 16. For the size of the cross section of the small space, the diameter is preferably 100 μm or more and 1,000 μm or less. The nozzle 16 is in communication with the pump mechanism 14 through a pipe 17. The pipe 17 may be made of a conductive material or a non-conductive material. Furthermore, the nozzle 16 is electrically connected to the high-voltage power source 12. This allows high voltage to be applied to the nozzle 16. In this case, the nozzle 16 is electrically connected to the high-voltage power source 12 through a current limiting resistor 19 to avoid excessive flow of current when the nozzle directly comes in contact with the human body.

The pump mechanism 14 in communication with the nozzle 16 through the pipe 17 functions as a unit for supplying the pump mechanism 14 stored in the container 15 to the nozzle 16. The pump mechanism 14 operates when power is supplied thereto from the low-voltage power source 11. The pump mechanism 14 is controlled by the auxiliary electronic circuit 13 to supply a predetermined amount of the composition for spraying to the nozzle 16.

The container 15 is connected to the pump mechanism 14 through a flexible pipe 18. The container 15 stores the composition for spraying. A gear pump mechanism and a piston pump mechanism are preferred as the pump mechanism 14.

It is preferable that the container 15 be in the form of an exchangeable cartridge.

Figure 2:
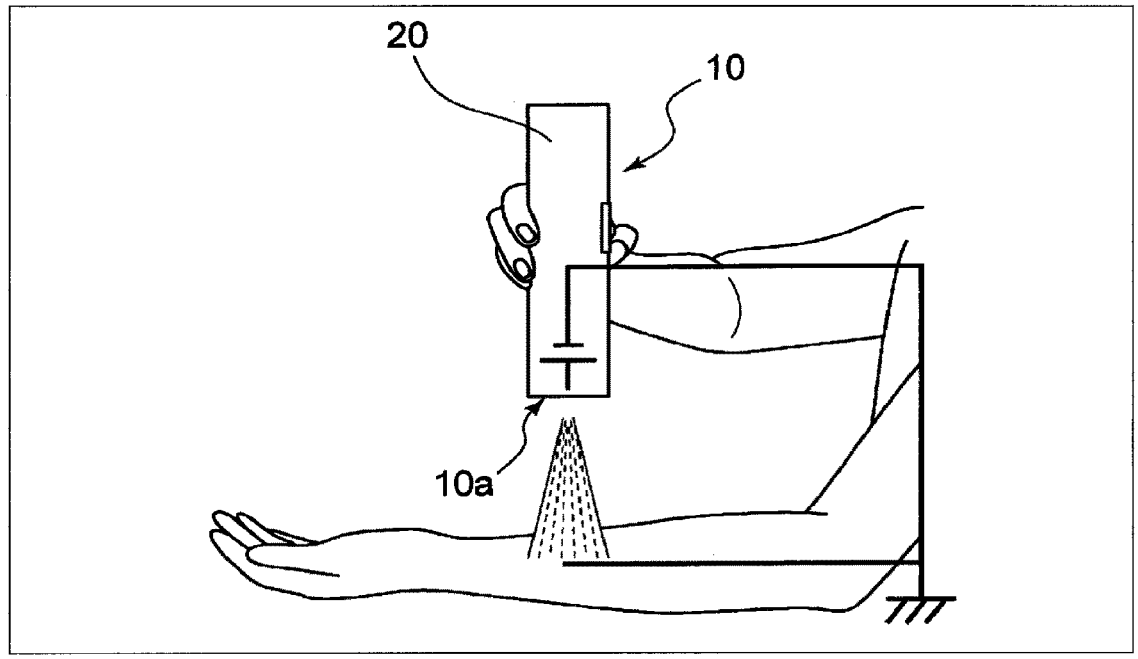
FIG. 2 is a schematic view showing a state in which an electrostatic spraying method is performed using an electrostatic spraying apparatus.

The electrostatic spraying apparatus 10 having the above structure may be used in the manner, for example, as described in FIG. 2. FIG. 2 shows a handheld electrostatic spraying apparatus 10 with a size which can be carried in one hand. In the electrostatic spraying apparatus 10 in the figure, all members shown in the structural view of FIG. 1 are stored in a cylindrical housing 20. A nozzle (not shown) is arranged at an end 10a in the longitudinal direction of the housing 20. The nozzle is arranged in the housing 20 so that the direction of discharge of the composition matches the longitudinal direction of the housing 20 and the nozzle protrudes to the side of the skin, which is the target on which a coating film is formed. Because the tip of the nozzle is arranged in the longitudinal direction of the housing 20 so as to protrude to the target on which a coating film is formed, the composition for spraying is less likely to be attached to the housing, and thus a coating film can be formed in a stable manner.

When a coating film is to be formed on the skin of a user him/herself, the user, who operates the electrostatic spraying apparatus 10 to form the coating film on his/her skin using the electrostatic spray, holds the apparatus 10 by his/her hand, and directs one of the ends 10a of the apparatus 10, at which a nozzle (not shown) is arranged, to the target site of electrostatic spraying. FIG. 2 shows that one of the ends 10a of the electrostatic spraying apparatus 10 is directed to the inside of user's forearm. The apparatus 10 is turned on in that state to perform the electrostatic spraying method. When the apparatus 10 is turned on, an electric field occurs between the nozzle and the skin. In an embodiment shown in FIG. 2, high positive voltage is applied to the nozzle and the skin serves as a negative electrode. When an electric field occurs between the nozzle and the skin, the composition for spraying at the tip of the nozzle is polarized due to electrostatic induction, and the tip portion of the composition takes a conical shape, and then droplets of the composition for spraying charged are discharged to the air toward the skin from the tip of the cone along the electric field. As the component (a), which is a solvent, evaporates from the charged composition for spraying which has been discharged to the air, the charge density on the surface of the composition for spraying becomes excessively high, and while its particles are repeatedly made smaller due to the Coulomb repulsion, the composition spreads into the air and reaches the skin. Adjusting the viscosity of the composition for spraying to an appropriate viscosity at that stage allows the composition sprayed to reach the skin in the form of droplets. Alternatively, a volatile substance as the component (a), which is a solvent, evaporates from the composition when the composition is discharged into the air so that the polymer capable of forming a coating film, which is a solute, is solidified, and while the composition is expanded and deformed due to the potential difference, fiber may be formed and deposited on the surface of the skin. When, for example, the viscosity of the composition for spraying is increased, the composition is likely to be deposited on the surface of the skin in the form of fiber. This allows a coating film made of a deposit of fiber to be formed on the surface of the skin. The coating film made of a deposit of fiber may also be formed while adjusting the distance between the nozzle and the skin and the voltage to be applied to the nozzle.

During the electrostatic spraying method, large potential difference occurs between the skin, which is the target on which a coating film is to be formed, and the nozzle. However, due to significantly high impedance, only a small amount of current flows through the human body. The present inventors have verified that the current which flows through the human body in the electrostatic spraying method is a few orders of magnitude smaller than, for example, the current of static electricity which flows through the human body in daily lives.

When a deposit of fiber is formed by an electrostatic spraying method, the thickness of the fiber is preferably 10 nm or more, and more preferably 50 nm or more in the equivalent circle diameter. The thickness is preferably 3,000 nm or less, and more preferably 1,000 nm or less. The thickness of fiber may be measured by, for example, magnifying the fiber by 10,000 times and observing it by a scanning electron microscope (SEM), removing defects (aggregates of fiber, intersections of fiber and droplets) in the two-dimensional image, selecting optional 10 fibers, drawing a line perpendicular to the longitudinal direction of the fiber and directly measuring the diameter of the fiber.

Although the above fiber is a continuous fiber with an infinite length in the theory of production, it is preferable that the fiber have a length at least 100 times as much as the thickness of the fiber. In the present description, the fiber having a length 100 times or more the thickness of the fiber is defined as "continuous fiber." It is preferable that the coating film produced by the electrostatic spraying method be a porous non-continuous coating film made of a deposit of continuous fiber. The coating film in such a form is an aggregate and thus not only can be used as a sheet but also is very soft and has the advantage of not being broken into pieces even when shear force is applied thereto and having excellent followability to the body movement. The coating film also has the advantage of having excellent releasability of sweat from the skin. Another advantage is that such coating films are easily peeled off. By contrast, continuous coating films without pores are not easily peeled off, and since they have very small releasability of sweat, the skin is likely to get sweaty.

The composition for spraying which has been formed into fiber reaches the skin in a charged state. Since the skin is also charged as described above, the fiber adheres to the skin due to electrostatic force. In combination with an anchor effect caused by small irregularities such as texture formed on the surface of the skin, the fiber adheres more to the surface of the skin. After completing electrostatic spraying in that way, the electrostatic spraying apparatus 10 is turned off. Then the electric field between the nozzle and the skin disappears and the electric charge on the surface of the skin is immobilized. As a result, the coating film becomes more adhesive.

Although the above describes a porous coating film made of a deposit of fiber, the form of the coating film is not limited thereto. A continuous coating film without pores may be formed; for example, a porous coating film in the form other than the deposit of fiber, e.g., a porous coating film prepared by forming a plurality of through holes irregularly or regularly in a continuous coating film, i.e., a non-continuous coating film, may also be formed. As described above, a coating film having any shape may be formed by controlling the viscosity of the composition for spraying, the distance between the nozzle and the skin, and the voltage applied to the nozzle.

The distance between the nozzle and the skin depends on the voltage applied to the nozzle, and is preferably 50 mm or more and 150 mm or less in order to form a coating film successfully. The distance between the nozzle and the skin may be measured by a commonly used non-contact sensor.

The basis weight of the coating film is preferably 0.1 $g/m^2$ or more, and more preferably 1 $g/m^2$ or more regardless of whether the coating film formed by the electrostatic spraying method is porous or not. The basis weight of the coating film is preferably 30 $g/m^2$ or less, and more preferably 20 $g/m^2$ or less. The basis weight of the coating film is, for example, preferably 0.1 $g/m^2$ or more and 30 $g/m^2$ or less, and more preferably 1 $g/m^2$ or more and 20 $g/m^2$ or less. When the basis weight of the coating film is set as described above, adhesiveness of coating film can be improved. The electrostatic spraying step of electrostatically spraying a composition directly to the skin to form a coating film means a step of electrostatic spraying to the skin to form a coating film. The step of electrostatic spraying a composition to a site other than the skin to prepare a sheet made of fiber and then applying the sheet to the skin is different from the electrostatic spraying step.

Next, Step B will be described.

The Step B is a step of applying a composition Y other than the composition X (composition for spraying), which contains a component (c) and a component (d), to the skin. The Step B is performed before or after the electrostatic spraying step A:
  (c) 0.5% by mass or more and less than 5% by mass of an adhesive polymer;
  (d) one or more selected from the group consisting of a polyol and a liquid oil.

The Step B is a step of applying the composition Y to the skin by a unit other than electrostatic spraying.

The adhesive polymer (c) used for the composition Y contributes to improvement of adhesiveness and improvement of abrasion resistance of the coating film formed on the skin by electrostatic spraying after a lapse of a long time. A material usually used as an adhesive or a pressure-sensitive adhesive may be used as the adhesive polymer. Examples thereof include adhesive rubber polymers, adhesive silicone polymers, adhesive acrylic polymers and adhesive urethane polymers, and one or more selected therefrom may be used. Furthermore, at least one selected from the group consisting of a nonionic polymer, an anionic polymer, a cationic polymer and an amphoteric polymer may be used as the adhesive polymer (c). The adhesive polymer (c) is preferably a polymer other than the polymer as the component (b).

Examples of the adhesive rubber polymers include adhesive rubber polymers composed of, as a base polymer, natural rubber; or synthetic rubber such as polyisoprene rubber, styrene-butadiene (SB) rubber, styrene-isoprene (SI) rubber, styrene-isoprene-styrene block copolymer (SIS) rubber, styrene-butadiene-styrene block copolymer (SBS) rubber, styrene-ethylene-butylene-styrene block copolymer (SEBS) rubber, styrene-ethylene-propylene-styrene block copolymer (SEPS) rubber, styrene-ethylene-propylene block copolymer (SEP) rubber, regenerated rubber, butyl rubber, polyisobutylene and a modified product thereof.

Of the adhesive rubber polymers, at least one selected from the group consisting of styrene-isoprene-styrene block copolymer, styrene-butadiene-styrene block copolymer, styrene-butadiene rubber, polyisobutylene, isoprene rubber and silicone rubber is more preferable. Examples of a commercially available adhesive rubber polymer include YODOSOL GH41F made by AkzoNobel.

Examples of the adhesive acrylic polymers include adhesive acrylic polymers composed of, as a base polymer, an acrylic polymer (a homopolymer or a copolymer) prepared by using one or more (meth)acrylic acid alkyl esters as a monomer component. Specific examples of the (meth) acrylic acid alkyl esters include (meth)acrylic acid C1-20 alkyl esters such as methyl (meth)acrylate, ethyl (meth) acrylate, propyl (meth)acrylate, isopropyl (meth)acrylate, butyl (meth)acrylate, isobutyl (meth)acrylate, s-butyl (meth) acrylate, t-butyl (meth)acrylate, pentyl (meth)acrylate, hexyl (meth)acrylate, heptyl (meth)acrylate, octyl (meth)acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth)acrylate, dodecyl (meth)acrylate, tridecyl (meth) acrylate, tetradecyl (meth) acrylate, pentadecyl (meth) acrylate, hexadecyl (meth) acrylate, heptadecyl (meth) acrylate, octadecyl (meth)acrylate, nonadecyl (meth)acrylate and eicosyl (meth) acrylate.

Examples of secondary monomers used in combination with those base polymers include N-vinyl pyrrolidone, methyl vinyl pyrrolidone, (meth)acrylic acid and vinyl acetate. Examples of commercially available acrylic polymers include Amphomer 28-4910 (made by AkzoNobel), YODOSOL GH256F (particle size 20 to 40 nm, made by AkzoNobel), YODOSOL GH800F (made by AkzoNobel), YODOSOL GH810F (made by AkzoNobel), DAITOSOL 5000AD (made by DAITO KASEI KOGYO CO., LTD.) and DAITOSOL 5000SJ (made by DAITO KASEI KOGYO CO., LTD.)

Adhesive silicone polymers composed of, as a base polymer, for example, a silicone rubber or a silicone resin containing organopolysiloxane are preferably used as the adhesive silicone polymer. A base polymer prepared by cross-linking the above silicone rubber or silicone resin may be used as the base polymer constituting the adhesive silicone polymer. Examples of the silicone rubber include organopolysiloxane containing dimethylsiloxane as a structural unit. A functional group (e.g., vinyl group) may be introduced into organopolysiloxane as needed. Examples of the silicone resin include organopolysiloxane containing at least one structural unit selected from the group consisting of an $R_3SiO_{1/2}$ structural unit, $SiO_2$ structural unit, $RSiO_{3/2}$ structural unit and $R_2SiO$ structural unit. The adhesive silicone polymer may contain a cross-linking agent. Examples of the cross-linking agent include siloxane cross-linking agents and peroxide cross-linking agents. Any suitable peroxide cross-linking agent may be used as the peroxide cross-linking agent. Examples of the peroxide cross-linking agent include benzoyl peroxide, t-butyl peroxybenzoate and dicumyl peroxide. Examples of the siloxane cross-linking agent include polyorganohydrogensiloxane.

Poly(N-acylalkyleneimine)-modified organopolysiloxane described below (hereinafter also simply referred to as "modified organopolysiloxane") may be used as organopolysiloxane.

In the modified organopolysiloxane, a poly(N-acylalkyleneimine) segment composed of a repeat unit represented by the following formula (1):

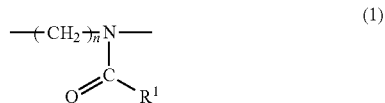

(1)

(in which $R^1$ represents a hydrogen atom, an alkyl group, aralkyl group or an aryl group having 1 to 22 carbon atoms and n represents 2 or 3) is bonded to at least two silicon atoms in the organopolysiloxane segment constituting the main chain through an alkylene group containing a heteroatom; the mass ratio of the organopolysiloxane segment (α) constituting the main chain to the poly(N-acylalkyleneimine) segment (β) (α/β) is 40/60 or more and 98/2 or less; and the organopolysiloxane segment constituting the main chain has a weight average molecular weight of 30,000 or more and 100,000 or less.

The mass ratio of the organopolysiloxane segment (a) to the poly(N-acylalkyleneimine) segment (β) (α/β) in the modified organopolysiloxane is preferably 40/60 or more, more preferably 55/45 or more, and further preferably 65/35 or more from the viewpoint of improvement of the abrasion resistance of coating film. The mass ratio is preferably 98/2 or less, more preferably 90/10 or less and further preferably 82/18 or less from the viewpoint of formation of coating film in the form of fiber.

In the modified organopolysiloxane, although at least two poly(N-acylalkyleneimine) segments may be bonded to any silicon atom constituting an organopolysiloxane segment through an alkylene group containing a heteroatom, it is preferable that the poly(N-acylalkyleneimine) segment be bonded to one or more silicon atoms excluding the silicon atom at both terminals through the above alkylene group. It is more preferable that the poly(N-acylalkyleneimine) segment be bonded to two or more silicon atoms excluding the silicon atom at both terminals through the above alkylene group.

Examples of the alkylene group containing a heteroatom, through which the organopolysiloxane segment and the poly(N-acylalkyleneimine) segment are bonded, include an alkylene group having 2 to 20 carbon atoms and containing 1 to 3 nitrogen atoms, oxygen atoms, and/or sulfur atoms. Specific examples thereof include the following:

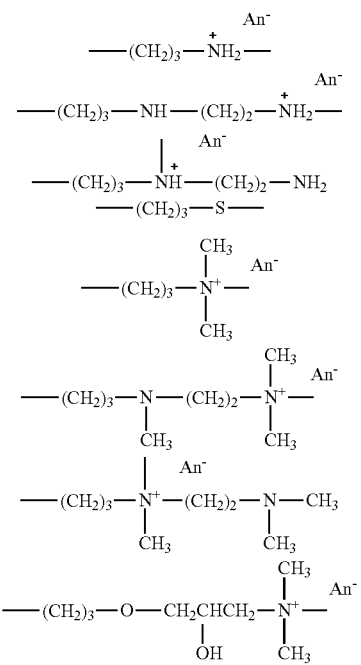

[In the formula, An⁻ represents an anion.]

The N-acylalkyleneimine unit constituting the poly(N-acylalkyleneimine) segment is represented by the formula (1). Examples of R', i.e., alkyl groups having 1 to 22 carbon atoms in the formula (1) include a linear, branched or cyclic alkyl group having 1 to 22 carbon atoms, such as a methyl group, an ethyl group, a n-propyl group, an isopropyl group, a n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group and a docosyl group.

Examples of the aralkyl group include aralkyl groups having 7 to 15 carbon atoms, such as a benzyl group, a phenethyl group, a trityl group, a naphthylmethyl group and an anthracenylmethyl group.

Examples of the aryl group include aryl groups having 6 to 14 carbon atoms, such as a phenyl group, a tolyl group, a xylyl group, a naphthyl group, a biphenyl group, an anthryl group and a phenanthryl group.

In the present description, the mass ratio (α/β) refers to a value determined from the integral ratio of alkyl groups or phenyl groups in the organopolysiloxane segment to methylene groups in the poly(N-acylalkyleneimine) segment obtained in nuclear magnetic resonance (¹H-NMR) analysis after dissolving 5% by mass of organopolysiloxane in deuterated chloroform.

In the modified organopolysiloxane, the organopolysiloxane segment between adjacent poly(N-acylalkyleneimine) segments has a weight average molecular weight (MWg) of preferably 1,300 or more, more preferably 1,500 or more, and further preferably 1,800 or more, and preferably 32,000 or less, more preferably 10,000 or less, and further preferably 5,000 or less.

In the present description, as shown in the following formula (2), the "organopolysiloxane segment between adjacent poly(N-acylalkyleneimine) segments" refers to a portion surrounded by the dotted line, which is between two bonding sites of a bonding site in a poly(N-acylalkyleneimine) segment to a organopolysiloxane segment (bonding site A) and a bonding site in a poly(N-acylalkyleneimine) segment adjacent thereto (bonding site B), and the segment is composed of an $R^2SiO$ unit, $R^6$, and $y+1$ $R^2_2SiO$ units. Furthermore, the "poly(N-acylalkyleneimine) segment" refers to $-Z-R^7$ bonding to the above $R^6$.

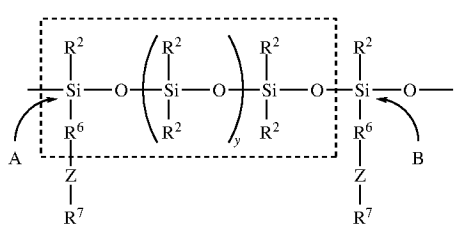

(2)

In the above formula (2), $R^e$s each independently represent an alkyl group having 1 to 22 carbon atoms or a phenyl group, $R^6$ represents an alkylene group having a heteroatom, $R^7$ represents a residue of a polymerization initiator, $-Z-R^7$ represents a poly(N-acylalkyleneimine) segment and y represents a positive number.

MWg, which is the molecular weight of the portion surrounded by the dotted line in the above formula (2), may be regarded as the mass of the organopolysiloxane segment (g/mole) per 1 mole of the poly(N-acylalkyleneimine) segment. When 100% of the functional groups in organopolysiloxane, which is a raw material compound, is substituted by poly(N-acylalkyleneimine), MWg is equal to the functional group equivalent weight (g/mole) of modified organopolysiloxane.

When the functional group equivalent weight (g/mole) of the raw material compound organopolysiloxane is known, MWg can be calculated by the following equation even when 100% of the functional groups is not substituted by poly(N-acylalkyleneimine).

MWg=[Functional group equivalent weight of organopolysiloxane (g/mole)]÷[substitution degree (%)/100(%)]

When the functional group equivalent weight of organopolysiloxane is unknown, MWg can be determined by the following equation using the ratio of the content of the organopolysiloxane segment constituting the main chain (Csi) and the molecular weight of the poly(N-acylalkyleneimine) segment (MWox).

$$MWg = \frac{Csi \times MWox}{100 - Csi}$$

While the molecular weight of the poly(N-acylalkyleneimine) segment (MWox) may be calculated from the molecular weight of the N-acylalkyleneimine unit and the polymerization degree, or measured by the gel permeation chromatography (GPC) method described later, the molecular weight of the poly(N-acylalkyleneimine) segment (MWox) in the present invention refers to a number average molecular weight measured by GPC. The modified organopolysiloxane has MWox of preferably 500 or more, more preferably 600 or more, and further preferably 700 or more, and preferably 5,500 or less, more preferably 3,500 or less, and further preferably 3,000 or less from the viewpoint of excellent abrasion resistance.

The organopolysiloxane segment constituting the main chain has a weight average molecular weight (MWsi) of 7,000 or more, preferably 10,000 or more, and more preferably 20,000 or more, and 120,000 or less, preferably 80,000 or less, and more preferably 60,000 or less from the viewpoint of excellent abrasion resistance. Since the organopolysiloxane segment constituting the main chain has the same skeleton as the raw material compound, organopolysiloxane, MWsi is substantially the same as the weight average molecular weight of the raw material compound, organopolysiloxane. The weight average molecular weight of the raw material compound, organopolysiloxane is measured by GPC under the following measurement conditions and represented in terms of polystyrene.

Column: Super HZ4000+Super HZ2000 (made by TOSOH CORPORATION)
Eluent: 1 mM triethylamine/THF
Flow rate: 0.35 mL/min
Temperature of column: 40° C.
Detector: UV
Sample: 50 μL The modified organopolysiloxane has a weight average molecular weight (MWt) of preferably 10,000 or more, more preferably 12,000 or more, and further preferably 24,000 or more, and preferably 2,000,000 or less, more preferably 150,000 or less, further preferably 120,000 or less, still more preferably 92,000 or less, and yet more preferably 80,000 or less. This provides a coating film having sufficient film strength and excellent abrasion resistance. In the present description, MWt may be determined from the weight average molecular weight of the raw material compound, modified organopolysiloxane and the mass ratio (α/β) described above.

Modified organopolysiloxane may be produced by a known method, for example, the methods disclosed in JP-A-2009-024114 and International Publication No. 2011/062210.

Examples of the adhesive urethane polymers include those made of a urethane resin prepared by reacting a polyol and a polyisocyanate compound. Examples of the polyol include polyether polyol, polyester polyol, polycarbonate polyol and polycaprolactone polyol. Examples of the polyisocyanate compound include diphenylmethane diisocyanate, tolylene diisocyanate and hexamethylene diisocyanate. Examples of commercially available adhesive urethane polymers include Baycusan C2000 (COVESTRO AG).

The nonionic polymer is not particularly limited, and any nonionic polymer usually used in the field of cosmetics may be used. The liquid formulation may contain one or more nonionic polymers, and also one or more anionic, cationic and/or amphoteric polymers in combination with the nonionic polymer.

Examples of the nonionic polymer include nonionic water-soluble (meth)acrylic polymers, nonionic water-insoluble (meth)acrylic polymers, polyvinyl pyrrolidone, polyacrylamide, low-saponified polyvinyl alcohol (saponification degree of 60% by mole or less), a neutral polysaccharide and a derivative thereof (e.g., an ether or ester thereof). Examples of the neutral polysaccharide and a derivative thereof include neutral gums (e.g., guar gum, hydroxypropyl guar), cellulose ether (hydroxyethylcellulose (HEC), methylhydroxyethylcellulose (MHEC), ethylhydroxyethylcellulose (EHEC), methylethylhydroxyethylcellulose (MEHEC), hydroxypropylcellulose (HPC), hydroxypropylmethylcellulose (HPMC), a hydrophobized derivative thereof (e.g., HM-EHEC)), and starch and a derivative thereof (e.g., dextrin).

Examples of compounds having an ethylenically unsaturated bond and capable of forming a nonionic polymer, such as nonionic water-soluble (meth)acrylic polymers, nonionic water-insoluble (meth)acrylic polymers, polyvinyl pyrrolidone, polyacrylamide and low-saponified polyvinyl alcohol (saponification degree of 60% by mole or less) described above will be listed below, but the present invention is not limited by the following specific examples.

Examples of nonionic monomers include (meth)acrylic acid esters such as methyl(meth)acrylate, ethyl (meth)acrylate, n-propyl (meth)acrylate, isopropyl (meth)acrylate, n-butyl (meth)acrylate, isobutyl (meth) acrylate, t-butyl (meth) acrylate, n-pentyl (meth)acrylate, n-hexyl (meth) acrylate, cyclohexyl (meth) acrylate, n-heptyl (meth) acrylate, n-octyl (meth)acrylate, 2-ethylhexyl (meth)acrylate, nonyl (meth)acrylate, decyl (meth)acrylate, dodecyl (meth) acrylate, phenyl (meth)acrylate, toluyl (meth)acrylate, benzyl (meth)acrylate, isobornyl (meth)acrylate, 2-methoxyethyl (meth)acrylate, 3-methoxybutyl (meth) acrylate, 2-hydoxyethyl (meth) acrylate, 2-hydroxypropyl (meth) acrylate, stearyl (meth) acrylate, glycidyl (meth)acrylate, 2-aminoethyl (meth)acrylate, γ-((meth)acryloyloxypropyl) trimethoxysilane, γ-((meth)acryloyloxypropyl)dimethoxymethylsilane, an ethylene oxide adduct of (meth) acrylic acid, trifluoromethylmethyl (meth) acrylate, 2-trifluoromethylethyl (meth) acrylate, 2-perfluoroethylethyl (meth) acrylate, 2-perfluoroethyl-2-perfluorobutylethyl (meth) acrylate, 2-perfluoroethyl (meth) acrylate, perfluoromethyl (meth) acrylate, diperfluoromethylmethyl (meth) acrylate, 2-perfluoromethyl-2-perfluoroethylmethyl (meth) acrylate, 2-perfluorohexylethyl (meth) acrylate, 2-perfluorodecylethyl (meth)acrylate and 2-perfluorohexadecylethyl (meth)acrylate; aromatic alkenyl compounds such as styrene, α-methylstyrene, p-methylstyrene and p-methoxystyrene; vinyl cyanide compounds such as acrylonitrile and methacrylonitrile; conjugated diene compounds such as butadiene and isoprene; halogen-containing unsaturated compounds such as vinyl chloride, vinylidene chloride, perfluoroethylene, perfluoropropylene and vinylidene fluoride; silicon-containing unsaturated compounds such as vinyl trimethoxysilane and vinyltriethoxysilane; unsaturated carboxylic anhydride such as maleic anhydride; unsaturated dicarboxylic acid diesters such as maleic acid dialkyl ester and fumaric acid dialkyl ester; vinyl ester compounds such as vinyl acetate, vinyl propionate, vinyl pivalate, vinyl benzoate and vinyl cinnamate; maleimide compounds such as maleimide, N-methylmaleimide, N-ethylmaleimide, N-propylmaleimide, N-butylmaleimide, N-hexylmaleimide, N-octylmaleimide, N-dodecylmaleimide, N-stearylmaleimide, N-phenylmaleimide and N-cyclohexylmaleimide; monomers derived from (meth)acrylic acid or (meth)acrylamide and alkylene oxide having 2 to 4 carbon atoms, such as polyethylene glycol (meth)acrylate, methoxypoly(ethylene glycol/propylene glycol) mono(meth)acrylate, polyethylene glycol di(meth)acrylate and N-polyalkylenoxy(meth) acrylamide; and hydrophilic nonionic monomers such as N-vinyl pyrrolidone, N-(meth)acryloylmorpholine and acrylamide.

Of them, one or more selected from the group consisting of a nonionic water-insoluble (meth)acrylic polymer, polyvinyl pyrrolidone and low-saponified polyvinyl alcohol (saponification degree of 60% by mole or less) are preferred. Examples of commercially available products thereof include MAS683 (made by CosMED Pharmaceutical Co., Ltd.), polyvinyl pyrrolidone K-90 (made by BASF) and JMR-150L (JAPAN VAM & POVAL CO. LTD.).

In the present description, the term "(meth)acrylic" means "acrylic or methacrylic."

The anionic polymer is not particularly limited, and any anionic polymer usually used in the field of cosmetics may be used. The liquid formulation may contain one or more anionic polymers, and also one or more nonionic, cationic and/or amphoteric polymers in combination with the anionic polymer.

Examples of the anionic polymers include anionic polysaccharides and derivatives thereof (e.g., alginate, pectin, hyaluronate), anionic gums (e.g., xanthan gum, dehydroxanthan gum, hydroxypropylxanthan gum, gum arabic, karaya gum, tragacanth gum), anionic cellulose derivatives (e.g., carboxymethylcellulose (CMC)), anionic water-soluble (meth)acrylic polymers and anionic water-soluble acrylamide polymers.

Examples of compounds having an ethylenically unsaturated bond and capable of forming an anionic polymer, such as anionic water-soluble (meth)acrylic polymer described above will be listed below, but the present invention is not limited by the following specific examples. Examples of anionic monomers include unsaturated carboxylic acid compounds such as (meth)acrylic acid, maleic acid, maleic anhydride, itaconic acid, fumaric acid and crotonic acid; partial ester compounds of unsaturated polybasic acid anhydride (e.g., succinic anhydride, phthalic anhydride) and hydroxyl group-containing (meth)acrylate (e.g., hydroxyethyl (meth)acrylate); sulfonic acid group-containing compounds such as styrene sulfonic acid and sulfoethyl (meth) acrylate; phosphoric acid group-containing compounds such as acid phosphoxyethyl (meth)acrylate. These anionic unsaturated monomers may be directly used in the form of acid, or used after being partially or completely neutralized. Alternatively, they may be copolymerized in the form of acid and then partially or completely neutralized. Examples of basic compounds used for neutralization include alkali metal hydroxides such as potassium hydroxide and sodium hydroxide, and amine compounds such as ammonia water, mono-, di-, tri-ethanolamine, and trimethylamine.

Of them, anionic water-insoluble acrylic polymers are particularly preferred. Examples of commercially available products thereof include MASCOS10 (made by CosMED Pharmaceutical Co., Ltd.) and HiPAS10 (made by CosMED Pharmaceutical Co., Ltd.).

Furthermore, an emulsion thickener containing those nonionic polymer and/or anionic polymer may also be used. Examples thereof include polyacrylamide/(C13,C14) isoparaffin/laureth-7 (Sepigel 305 made by Seppic).

The cationic polymer is not particularly limited, and any cationic thickening polymer usually used in the field of cosmetics may be used. The liquid formulation may contain one or more cationic polymers, and also one or more nonionic, anionic and/or amphoteric polymers in combination with the cationic polymer.

Cationic polymers have a cationic group such as a quaternary ammonium group or a primary, secondary or tertiary amino group which can be ionized to be a cationic group. Typically a cationic polymer contains an amine group or an ammonium group in the side chain of the polymer chain, or contains a diallyl quaternary ammonium salt as a structural unit.

Examples of preferred cationic polymers include a cationized cellulose, cationic starch, cationic guar gum, vinyl or (meth)acrylic polymer or copolymer having a quaternary ammonium side chain, a quaternized polyvinyl pyrrolidone, a (meth)acrylate/aminoacrylate copolymer, an amine-substituted poly(meth)acrylate crosspolymer, a cationic water-soluble (meth)acrylic polymer and a cationic water-soluble acrylamide polymer.

Examples of compounds having an ethylenically unsaturated bond and capable of forming a cationic polymer, such as cationic water-soluble (meth)acrylic polymer described above will be listed below, but the present invention is not limited by the following specific examples. Examples of cationic monomers include cationic monomers prepared by cationizing, for example, N,N-dimethylaminoethyl (meth) acrylate, N,N-diethylaminoethyl (meth) acrylate, N,N-dimethylaminopropyl (meth) acrylate, N,N-diethylaminopropyl (meth) acrylate, N,N-dimethylaminoethyl (meth) acrylamide, N,N-diethylaminoethyl (meth) acrylamide, N,N-dimethylaminopropyl (meth) acrylamide, N,N-diethylaminopropyl (meth) acrylamide, p-dimethylaminomethylstyrene, p-dimethylaminoethylstyrene, p-diethylaminomethylstyrene and p-diethylaminoethylstyrene with a cationizing agent (e.g., halogenated alkyl such as methyl chloride, methyl bromide and methyl iodide, a dialkyl sulfuric acid such as dimethylsulfuric acid, an epichlorohydrin adduct of a tertiary amine mineral acid salt such as N-(3-chloro-2-hydroxypropyl)-N,N,N-trimethylammonium chloride, an inorganic salt of hydrochloric acid, hydrobromic acid, sulfuric acid, phosphoric acid, and the like, and a carboxylic acid such as formic acid, acetic acid and propionic acid).

Specific examples of the cationized cellulose include a polymer of a quaternary ammonium salt prepared by adding glycidyl trimethylammonium chloride to hydroxyethyl cellulose (polyquaternium-10), hydroxyethyl cellulose/dimethyldiallylammonium chloride copolymer (polyquaternium-4), and a polymer of a quaternary ammonium salt prepared by reacting hydroxyethyl cellulose with trimethylammonium-substituted epoxide and lauryldimethylammonium-substituted epoxide (polyquaternium-67).

Examples of the vinyl or (meth)acrylic polymer or copolymer having a quaternary ammonium side chain include poly(2-methacryloxyethyl trimethylammonium chloride) (polyquaternium-37).

Specific examples of the quaternized polyvinyl pyrrolidone include quaternary ammonium salt synthesized from a copolymer of vinyl pyrrolidone (VP) and dimethylaminoethyl methacrylate and diethyl sulfate (polyquaternium-11).

Examples of the (meth)acrylate/aminoacrylate copolymer include (acrylate/aminoacrylate/C10-30 alkyl PEG-20 itaconic acid) copolymer.

Examples of the amine-substituted poly(meth)acrylate crosspolymer include polyacrylate-1 crosspolymer and polyquaternium-52.

Of them, cationic water-soluble acrylamide polymers are particularly preferred. Examples of commercially available products thereof include t-butyl acrylamide/ethyl acrylate/dimethylaminopropyl acrylamide/methoxypolyethylene glycol methacrylate copolymer (RP77S made by KAO CORPORATION).

Amphoteric polymers have both a cationic group and an anionic group. From the viewpoint of structure, the amphoteric polymer can be derived from any of the above cationic polymers by further introducing an anionic group or a comonomer into the cationic polymer.

Any amphoteric polymer usually used in the field of cosmetics may be used. The liquid formulation may contain one or more amphoteric polymers, and also one or more nonionic, anionic and/or cationic polymers in combination with the amphoteric polymer.

Examples of the amphoteric polymer include carboxyl-modified or sulfonic acid-modified cationic polysaccharide (e.g., carboxymethyl chitosan), (meth)acrylate polymer having a phosphobetaine group or a sulfobetaine group in the side chain and amphoteric ion (meth)acrylic polymer.

Examples of compounds having an ethylenically unsaturated bond and capable of forming an amphoteric polymer such as amphoteric ion (meth)acrylic polymer described above will be listed below, but the present invention is not limited by the following specific examples. Specific examples of the amphoteric ion monomer include compounds prepared by allowing a modifying agent such as sodium haloacetate or potassium haloacetate to act on the aforementioned specific examples of cationic monomer precursors. Specific examples of polar monomers include amine oxides such as N,N-dimethylaminoethyl (meth) acrylate, N,N-diethylaminoethyl (meth) acrylate, N,N-dimethylaminopropyl (meth) acrylate, N,N-diethylaminopropyl (meth) acrylate, N,N-dimethylaminoethyl (meth) acrylamide, N,N-diethylaminoethyl (meth) acrylamide, N,N-dimethylaminopropyl (meth) acrylamide, N,N-diethylaminopropyl (meth)acrylamide, vinyl N,N-dimethylaminopropionate, p-dimethylaminomethylstyrene, p-dimethylaminoethylstyrene, p-diethylaminomethylstyrene and p-diethylaminoethylstyrene.

Other examples include a copolymer of cationic vinyl or (meth)acrylic monomer and (meth)acrylic acid (e.g., dimethyldiallylammonium chloride/acrylic acid copolymer (polyquaternium-22)).

A polymer having good adhesion is selected as the adhesive polymer (c) from the viewpoint of improvement of durability of coating film after a lapse of a long time. As the adhesive polymer, a polymer having a maximum tensile shear load measured in accordance with JIS K 6850 of 1 N or more is preferred, a polymer having that of 3N or more is more preferred, and a polymer having that of 5 N or more is further preferred. A polymer having a maximum tensile shear load measured in accordance with JIS K 6850 of 90 N or less is preferred, a polymer having that of 60 N or less is more preferred, and a polymer having that of 30 N or less is further preferred.

More specifically, it is preferable to use one or more selected from the group consisting of an adhesive rubber polymer, an adhesive silicone polymer, an adhesive acrylic polymer and an adhesive urethane polymer. Furthermore, it is preferable to use at least one selected from the group consisting of a nonionic polymer, an anionic polymer, a cationic polymer and an amphoteric polymer.

The adhesion of the polymer (maximum tensile shear load) may be measured as follows. 20 mg of a polymer solution (10% ethanol solution) is applied to an end of a piece of a polycarbonate substrate in an area of 1.25 cm×2.5 cm. The substrate is bonded to another polycarbonate (Carboglass Polish Clear made by Standard Test Piece Inc., 10 cm×2.5 cm×2.0 mm) substrate and the same is dried for 12 hours or more. Both ends of the polycarbonate substrate is pulled at a tensile rate of 5 mm/minute using TENSILON UTC-100W made by Orientec Co., Ltd. to measure maximum tensile shear load.

The content of the adhesive polymer (c) in the composition Y is 0.5% by mass or more and less than 5% by mass from the viewpoint of feeling and durability for crack or coming off of the coating film after a lapse of a long time. The content is more preferably 0.6% by mass or more, and further preferably 0.8% by mass or more. The content is preferably 4% by mass or less, more preferably 3% by mass or less, and further preferably 2% by mass or less. More specifically, the content is preferably 0.6% by mass or more and 4% by mass or less, more preferably 0.8% by mass or more and 3% by mass or less, and further preferably 0.8% by mass or more and 2% by mass or less.

The component (d) used for the composition Y is one or more selected from the group consisting of a polyol and a liquid oil (liquid at 20° C.). Examples of the polyol include an alkylene glycol such as ethylene glycol, propylene glycol, 1,3-propanediol and 1,3-butanediol; a polyalkylene glycol such as diethylene glycol, dipropylene glycol, polyethylene glycol having a molecular weight of 1,000 or less and polypropylene glycol; and a glycerol such as glycerol, diglycerol and triglycerol. Of them, ethylene glycol, propylene glycol, 1,3-butanediol, dipropylene glycol, polyethylene glycol having a molecular weight of 1,000 or less, glycerol and diglycerol are preferred, and propylene glycol, 1,3-butanediol and glycerol are more preferred from the viewpoint of feeling on use including smoothness when applied and durability after a lapse of a long time. It is further preferred that the polyol includes at least glycerol.

The liquid oil in the present invention refers to an oil which is in a liquid state at 20° C., and also includes a flowable semi-solid oil. Examples of the liquid oil include a hydrocarbon oil, an ester oil, a higher alcohol, a silicone oil and a fatty acid. Of them, a hydrocarbon oil, an ester oil, and a silicone oil are preferred from the viewpoint of smoothness when applied and adhesiveness and abrasion resistance after a lapse of a long time. One selected from the group consisting of those liquid oils may be used, or two or more thereof may be used in combination.

Examples of the liquid hydrocarbon oil described above include liquid paraffin, squalane, squalene, n-octane, n-heptane, cyclohexane, light isoparaffin, liquid isoparaffin, hydrogenated polyisobutene, polybutene and polyisobutene. From the viewpoint of feeling on use, liquid paraffin, light isoparaffin, liquid isoparaffin, squalane, squalene, n-octane, n-heptane and cyclohexane are preferred, and liquid paraffin and squalane are more preferred. From the viewpoint of adhesiveness and abrasion resistance of coating film electrostatically sprayed, the hydrocarbon oil preferably has a viscosity at 30° C. of 1 mPa·s or more, more preferably 3 mPa·s or more. From the viewpoint of adhesiveness and abrasion resistance of coating film, the total content of isododecane, isohexadecane and hydrogenated polyisobutene in the liquid formulation is preferably 10% by mass or less, more preferably 5% by mass or less, further preferably 1% by mass or less, and still more preferably 0.5% by mass or less. No hydrocarbon oil may be included.

Likewise, from the viewpoint of adhesiveness and abrasion resistance of coating film electrostatically sprayed, an ester oil and a silicone oil have a viscosity at 30° C. of preferably 1 mPa·s or more, and more preferably 3 mPa·s or more.

Herein the viscosity is measured by a BM-type viscometer (made by TOKIMEC Co., Ltd., measurement condition: rotor No. 1, 60 rpm, 1 minute) at 30° C. The total content of ether oils such as cetyl-1,3-dimethylbutyl ether, dicapryl ether, dilauryl ether and diisostearyl ether in the liquid formulation is preferably 10% by mass or less, more preferably 5% by mass or less and further preferably 1% by mass or less from the same viewpoint.

Examples of the ester oil described above include an ester composed of a linear or branched fatty acid and a linear or branched alcohol or a polyhydric alcohol. Specific examples thereof include isopropyl myristate, cetyl isooctanoate, isocetyl octanoate, octyldodecyl myristate, isopropyl palmitate, butyl stearate, hexyl laurate, decyl oleate, octyldodecyl oleate, hexyldecyl dimethyloctanoate, cetyl lactate, myristyl lactate, lanolin acetate, isocetyl stearate, isocetyl isostearate, ethylhexyl isononanoate, isononyl isononanoate, isotridecyl isononanoate, isostearyl isostearate, cholesteryl 12-hydroxystearate, ethylene glycol di-2-ethylhexanoate, dipentaerythritol fatty acid ester, N-alkylglycol monoisostearate, propylene glycol dicaprylate, propylene glycol diisostearate, neopentyl glycol dicaprate, diisostearyl malate, glycerol di-2-heptylundecanoate, trimethylol propane tri-2-ethylhexanoate, trimethylol propane triisostearate, pentaerythritol tetra-2-ethylhexanoate, glyceryl tri-2-ethylhexanoate, trimethylol propane triisostearate, cetyl 2-ethylhexanoate, 2-ethylhexyl palmitate, diethylhexyl naphthalenedicarboxylate, alkyl benzoate (having 12 to 15 carbon atoms), cetearyl isononanoate, glycerol tri(caprylate-caprate), butylene glycol(dicaprylate/caprate), propylene glycol di(caprylate/caprate), glyceryl triisostearate, glyceryl tri-2-heptylundecanoate, glyceryl tricocoate, castor oil fatty acid methyl ester, oleyl oleate, 2-heptylundecyl palmitate, diisobutyl adipate, N-lauroyl-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, di-2-ethylhexyl succinate, triethyl citrate, 2-ethylhexyl paramethoxycinnamate and tripropylene glycol dipivalate.

Of them, from the viewpoint of adhesion of coating film electrostatically sprayed onto the skin and excellent feeling when applied to the skin, one selected from the group consisting of octyldodecyl myristate, myristyl myristate, isocetyl stearate, isononyl isononanoate, isocetyl isostearate, cetearyl isononanoate, diisobutyl adipate, di-2-ethylhexyl sebacate, isopropyl mirystate, isopropyl palmitate, diisostearyl malate, neopentyl glycol dicaprate and glycerol tri (caprylate·caprate) is preferred, at least one selected from the group consisting of isopropyl myristate, isopropyl palmitate, diisostearyl malate, neopentyl glycol dicaprate, alkyl benzoate (having 12 to 15 carbon atoms) and glycerol tri(caprylate·caprate) is more preferred, and at least one selected from the group consisting of neopentyl glycol dicaprate and glycerol tri(caprylate·caprate) is further preferred.

A vegetable oil and an animal oil containing the above ester oil may be used as an ester oil. Examples thereof include olive oil, jojoba oil, macadamia nut oil, meadowfoam oil, castor oil, safflower oil, sunflower oil, avocado oil, canola oil, apricot kernel oil, rice germ oil, and rice bran oil.

Examples of the higher alcohol include liquid higher alcohols having 12 to 20 carbon atoms. A higher alcohol composed of a branched fatty acid is preferred, and specific examples thereof include isostearyl alcohol and oleyl alcohol.

Examples of a liquid silicone oil include a linear silicone, a cyclic silicone and a modified silicone, such as dimethylpolysiloxane, dimethylcyclopolysiloxane, methylphenylpolysiloxane, methylhydrogenpolysiloxane, phenyl-modified silicone and higher alcohol-modified organopolysiloxane.

The content of the silicone oil in the component (d) is preferably 35% by mass or less from the viewpoint of adhesiveness of coating film, and more preferably 10% by mass or less, further preferably 1% by mass or less, and still more preferably 0.1% by mass or less from the viewpoint of improvement of peeling properties.

The silicone oil has a dynamic viscosity at 25° C. of preferably 3 mm$^2$/s or more, more preferably 4 mm$^2$/s or more, and further preferably 5 mm$^2$/s or more, and preferably 30 mm$^2$/s or less, more preferably 20 mm$^2$/s or less, and further preferably 10 mm$^2$/s or less from the viewpoint of adhesiveness and abrasion resistance of coating film electrostatically sprayed.

It is preferable that of them, the silicone oil contain dimethylpolysiloxane from the viewpoint of adhesiveness and abrasion resistance of coating film electrostatically sprayed.

Furthermore, an oil agent in a solid state at 20° C. (solid oil) may be used. An oil agent which is in a solid state at 20° C. and has a melting point of 40° C. or more is preferred as the oil agent in a solid state at 20° C. Examples of the oil agent which is in a solid state at 20° C. include hydrocarbon wax, ester wax, a paraoxybenzoate, a higher alcohol, a linear fatty acid ester having 14 or more carbon atoms, a triglyceride composed of three linear fatty acids having 12 or more carbon atoms, and silicone wax. One or more selected therefrom may be included. The wax is not particularly limited as long as it is used for usual cosmetics. Examples thereof include mineral wax such as ozocerite and ceresin; petroleum wax such as paraffin, microcrystalline wax and petrolatum; synthetic hydrocarbon wax such as Fischer-Tropsch wax and polyethylene wax; plant wax such as carnauba wax, *Euphorbia cerifera* wax, rice bran wax, Japan wax, sunflower wax and hydrogenated jojoba oil; animal wax such as beeswax and whale wax; synthetic wax such as silicone wax, fluorine wax and synthetic beeswax; a fatty acid, a higher alcohol and a derivative thereof. Examples of the paraoxybenzate include methyl paraoxybenzoate, ethyl p-aminobenzoate, isobutyl paraoxybenzoate, isopropyl paraoxybenzoate, ethyl paraoxybenzoate, butyl paraoxybenzoate, propyl paraoxybenzoate and benzyl paraoxybenzoate. Examples of the triglyceride composed of three linear fatty acids having 12 or more carbon atoms include glyceryl trilaurate, glyceryl trimyristate, glyceryl tripalmitate and glyceryl tribehenate. Examples of a fatty acid ester oil composed of a linear fatty acid having 14 or more carbon atoms include myristyl myristate.

The content of the component (d) in the composition Y is preferably 1% by mass or more and 40% by mass or less, more preferably 2% by mass or more and 25% by mass or less, further preferably 4% by mass or more and 20% by mass or less, and still more preferably 10% by mass or more and 20% by mass or less from the viewpoint of improvement of adhesiveness, feeling and durability after a lapse of a long time of coating film.

The mass ratio of the component (d) to the component (c) in the composition Y is preferably 1 or more and 30 or less, more preferably 1 or more and 25 or less, and further preferably 3 or more and 20 or less from the viewpoint of durability of coating film after a lapse of a long time.

It is preferable that the composition Y contain both a polyol and a liquid oil from the viewpoint of durability of coating film after a lapse of a long time. The mass ratio of the polyol to the liquid oil (liquid at 20° C.) (polyol/liquid oil (liquid at 20° C.)) is preferably 0.4 or more and 40 or less, more preferably 1 or more and 20 or less, and further preferably 2 or more and 10 or less.

The composition Y may also contain a surfactant, a water-soluble polymer, an antioxidant, a flavoring agent, a coloring, an antiseptic, a pH adjuster, a blood circulation promoter, a cooling agent, an antiperspirant, a disinfectant, a skin activator, a moisturizer, a refrigerant and the like in addition to the above components. Examples of the surfactant include a nonionic surfactant, a cationic surfactant, an anionic surfactant and an amphoteric surfactant. Although the form of the composition Y may be an oil-in-water emulsion composition or a water-in-oil emulsion composition, a water-in-oil emulsion composition is preferred from the viewpoint of durability of coating film after a lapse of a long time.

The step of applying a composition Y to the skin (Step B) may be performed before or after the Step A. Furthermore, the unit for applying the composition Y to the skin is optional as long as it is other than electrostatic spraying. Examples thereof include applying it to the skin by the fingers and applying it to the skin using an applicator.

Makeup may also be applied to the skin before, between or after the Step A and the Step B by applying a cosmetic containing a powder to the skin (Step C). For example, the steps may be performed in the order of the Step A, the Step B and the Step C, or the Step B, Step A and the Step C. It is also preferable that the Step C be performed by a unit other than the electrostatic spraying.

Examples of the powder used for the cosmetic in the Step C include a color pigment, an extender, a pearl pigment and an organic powder. Examples of the color pigment include an inorganic color pigment, an organic color pigment and an organic dye, and one or more thereof may be used.

Specific examples of the inorganic color pigment include an inorganic colored pigment such as red iron oxide, iron hydroxide, iron titanate, yellow iron oxide, black iron oxide, carbon black, dark blue, ultramarine blue, dark blue titanium oxide, black titanium oxide, sintered products of titanium and titanium oxide, manganese violet, cobalt violet, chromium oxide, chromium hydroxide, cobalt oxide and cobalt titanate; and an inorganic white pigment such as titanium oxide, zinc oxide, calamine, zirconium oxide, magnesium oxide, cerium oxide, aluminum oxide and a composite thereof. One or more thereof may be used.

Of them, at least one or more selected from the group consisting of iron oxide, titanium oxide and zinc oxide are preferred, and one or more selected from the group consisting of titanium oxide, zinc oxide, red iron oxide, yellow iron oxide and black iron oxide are more preferred.

Examples of the organic color pigment and organic dye include organic tar pigments such as red No. 3, red No. 102, red No. 104, red No. 106, red No. 201, red No. 202, red No. 204, red No. 205, red No. 220, red No. 226, red No. 227, red No. 228, red No. 230, red No. 401, red No. 405, red No. 505, orange No. 203, orange No. 204, orange No. 205, yellow No. 4, yellow No. 5, yellow No. 401, blue No. 1 and blue No. 404; and organic dyes such as β-carotene, caramel, and paprika dyes. Furthermore, those coated with a polymer such as cellulose or polymethacrylic acid ester may be used. It is preferable that of them, at least red No. 102 be included.

Examples of the extender include barium sulfate, calcium sulfate, magnesium sulfate, magnesium carbonate, calcium carbonate, talc, mica, kaolin, sericite, silicic acid, silicic anhydride, aluminum silicate, magnesium silicate, magnesium aluminum silicate, calcium silicate, barium silicate, strontium silicate, metal tungstate, hydroxyapatite, vermiculite, clay, bentonite, montmorillonite, hectorite, smectite, zeolite, ceramic powder, calcium phosphate dibasic, alumina, silica, aluminum hydroxide, boron nitride, synthetic mica, synthetic sericite, metal soap and barium sulfate-treated mica. One or more thereof may be used.

It is preferable that of them, barium oxide, calcium carbonate, mica, silicic anhydride, talc, boron nitride and synthetic mica be included.

Examples of the pearl pigment (glitter powder) include fish foil, titanium oxide-coated mica (mica titanium), bismuth oxychloride, titanium oxide-coated bismuth oxychloride, titanium oxide-coated talc, titanium oxide-coated color mica, titanium oxide/iron oxide-coated mica, fine particulate titanium oxide-coated mica titanium, fine particulate zinc oxide-coated mica titanium, organic pigment-treated mica titanium, lower titanium oxide-coated mica, titanium oxide-coated synthetic mica, titanium oxide-coated plat-like silica, hollow plate-like titanium oxide, iron oxide-coated mica, plate-like iron oxide (MIO), aluminum flake, stainless flake, titanium oxide-coated plate-like alumina, glass flake, titanium oxide-coated glass flake, pearl shell, gold foil, gold-deposited resin film and metal-deposited resin film. One or more thereof may be used.

Examples of the organic powder include a silicone rubber powder, a silicone resin-coated silicone rubber powder, polymethylsilsesquioxane, a polyamide powder, a nylon powder, a polyester powder, a polypropylene powder, a polystyrene powder, a polyurethane powder, a vinyl resin powder, a urea resin powder, a phenolic resin powder, a fluorine resin powder, a silicon resin powder, an acrylic resin powder, a melamine resin powder, a polycarbonate resin, a divinylbenzene-styrene copolymer, a silk powder, a wool powder, a cellulose powder, a long-chain alkyl phosphoric acid metal salt, an N-mono long chain alkyl acyl basic amino acid, and a composite thereof. One or more thereof may be used.

It is preferable that of them, a cellulose powder, a silicone rubber powder, a silicone resin-coated silicone rubber powder, polymethylsilsesquioxane, an acrylic resin powder and a nylon powder be included.

All the powders used in the present invention may be directly used, or one or more thereof which have been hydrophobized may also be used. Methods of hydrophobization are not limited as long as they are usually done for a powder for a cosmetic. A dry process or a wet process may be performed using a surface treatment agent such as a fluorine compound, a silicone compound, metal soap, an amino acid compound, lecithin, alkylsilane, an oil agent and organic titanate.

Examples of the surface treatment agent include fluorine compounds such as perfluoropolyether, perfluoroalkyl phosphate ester, perfluoroalkylalkoxy silane and fluorine-modified silicone; silicone compounds such as dimethylpolysiloxane, methylhydrogenpolysiloxane, cyclic silicone, organopolysiloxane modified with a trialkoxy group at one or both terminals, a crosslinked silicone, a silicone resin, a fluorine-modified silicone resin and acryl-modified silicone; a metal soap such as aluminum stearate, aluminum myristate, zinc stearate and magnesium stearate; amino acid compounds such as proline, hydroxyproline, alanine, glycine, sarcosine, glutamic acid, aspartic acid, lysine and a derivative thereof; lecithin, hydrogenated lecithin; alkyl silane such as methyltrimethoxysilane, ethyltrimethoxysilane, hexyltrimethoxysilane, octyltrimethoxysilane and octyltriethoxysilane; oil agents such as polyisobutylene, wax and oil and fat; and organic titanate such as isopropyltitanium triisostearate.

A powder prepared by hydrophilizing one or more thereof may also be used as the powder used in the present invention. Methods of hydrophilization are not limited as long as they are usually done for a powder for a cosmetic.

Examples thereof include plant polymers such as gum arabic, tragacanth, arabinogalactan, locust bean gum (carob gum), guar gum, karaya gum, carrageenan, pectin, agar, quince seed (marmelo), starch (rice, corn, potato, wheat), algae colloid, trant gum and locust bean gum; microbial polymers such as xanthan gum, dextran, succinoglucan and pullulan; animal polymers such as collagen, casein, albumin, deoxyribonucleic acid (DNA) and a salt thereof; starch polymers such as carboxymethyl starch and methyl hydroxypropyl starch; cellulose polymers such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose and cellulose powder; alginic acid polymers such as sodium alginate and propylene glycol alginate ester; vinyl polymers such as polyvinyl methyl ether, polyvinyl pyrrolidone and carboxyvinyl polymer; polyoxyethylene polymers such as polyethylene glycol and polyethylene glycol silane; polyoxyethylene polyoxypropylene copolymers; acrylic polymers such as sodium polyacrylate, polyethylacrylate and polyacrylic acid amide; and inorganic silicic acid compounds such as silica.

A spherical, a plate-like, a needle-like or an amorphous powder, a fume or a particulate powder, a powder having a particle size of pigment grade, and a porous or a non-porous powder may be used as the powder, as long as they are usually used for cosmetics.

The powder has an average particle size of preferably 0.001 μm or more and 200 μm or less, more preferably 0.01 μm or more and 50 μm or less, further preferably 0.02 μm or more and 20 μm or less, and still more preferably 0.05 μm or more and 10 μm or less in order for the powder to adhere uniformly to the crista cutis, sulcus cutis and pores of the skin to create a natural feeling of make-up.

In the present invention, the average particle size of a powder is measured by a particle size distribution analyzer based on an observation with an electron microscope according to a laser diffraction/scattering method. More specifically, in the laser diffraction/scattering method, measurement is performed by a laser diffraction/scattering particle distribution analyzer (e.g., LMS-350 made by SEISHIN ENTERPRISE Co., Ltd.) using ethanol as a dispersion solvent. When a powder has been hydrophobized or hydrophilized, the average particle size and the content of the component (c) means the average particle size and the mass of a material including the hydrophobizing or hydrophilizing agent.

One or more powders may be used. The content thereof, which varies depending on the form of the cosmetic, is preferably 1% by mass or more, more preferably 3% by mass or more, further preferably 5% by mass or more, and preferably 99% by mass or less, more preferably 95% by mass or less, and further preferably 90% by mass or less in the cosmetic in consideration of finished look. The content of the powder is preferably 1% by mass or more and 99% by mass or less, more preferably 3% by mass or more and 95% by mass or less, and further preferably 5% by mass or more and 90% by mass or less in the cosmetic.

The mass ratio of the color pigment to the whole powder (color pigment/whole powder) is preferably 0.2 or more, more preferably 0.3 or more, and further preferably 0.4 or more, and preferably 1.0 or less in consideration of finished look and excellent durability over time of the cosmetic containing powder with little smudging.

The type of cosmetics used in the Step C is not particularly limited as long as it is a cosmetic containing a powder.

The cosmetic may be used as a cosmetic for makeup, such as a makeup base, a foundation, a concealer, a blush, an eye shadow, a mascara, an eyeliner, an eyebrow, an overcoating agent and a lipstick; and UV protection cosmetics such as a sunscreen emulsion and sunscreen cream. In particular, a makeup base, a foundation, a concealer, a sunscreen emulsion and a sunscreen cream are more preferred.

Furthermore, the form of cosmetics is not particularly limited, and the cosmetic may be any of a powder cosmetic, a solid powder cosmetic, a liquid cosmetic, an oil cosmetic, an emulsion cosmetic and a solid oil cosmetic.

Components included in the cosmetic used in the Step C other than the powder include an oil agent (including a liquid oil and a solid oil), an emulsifying agent, a water-soluble polymer, a flavoring agent, a repellent, an antioxidant, a stabilizer, an antiseptic, a thickener, a pH adjuster, a blood circulation promoter, vitamins, a cooling agent, an antiperspirant, a disinfectant, a skin activator and a moisturizer.

In the Step C the cosmetic may be applied to the skin by a usual unit of application other than electrostatic spraying depending on the type of cosmetics. Examples of the method of application include spreading and pressing using the fingers or the palm and spreading and pressing using a specific tool.

For the above embodiments, the present invention also discloses the following methods for producing a coating film and composition.

<1> A method for producing a coating film on the skin, comprising the steps of:
A) electrostatically spraying a composition X comprising a component (a) and a component (b) directly onto the skin to form a coating film on a surface of the skin:
(a) one or more volatile substances selected from the group consisting of water, an alcohol and a ketone;
(b) a polymer capable of forming a coating film; and
B) applying a composition Y other than the composition X comprising a component (c) and a component (d) to the skin
in the order presented or in reverse order:
(c) 0.5% by mass or more and less than 5% by mass of an adhesive polymer;
(d) one or more selected from the group consisting of a polyol and a liquid oil.

<2> The method for producing a coating film according to <1>, wherein the adhesive polymer (c) is one or more selected from the group consisting of an adhesive rubber polymer, an adhesive silicone polymer, an adhesive acrylic polymer and an adhesive urethane polymer, or at least one selected from the group consisting of a nonionic polymer, an anionic polymer, a cationic polymer and an amphoteric polymer, and the adhesive polymer is a polymer other than the polymer as the component (b).

<3> The method for producing a coating film according to <1> or <2>, wherein the adhesive polymer (c) has a maximum tensile shear load of preferably 1 N or more, more preferably 3 N or more, and further preferably 5 N or more.

<4> The method for producing a coating film according to any of <1> to <3>, wherein a content of the adhesive polymer (c) in the composition Y is preferably 0.6% by mass or more, and more preferably 0.8% by mass or more, and preferably 4% by mass or less, more preferably 3% by mass or less, and further preferably 2% by mass or less.

<5> The method for producing a coating film according to any of <1> to <4>, wherein the polyol (d) is preferably selected from the group consisting of an alkylene glycol such as ethylene glycol, propylene glycol, 1,3-propanediol and 1,3-butanediol; a polyalkylene glycol such as diethylene glycol, dipropylene glycol, a polyethylene glycol having a molecular weight of 1,000 or less and polypropylene glycol; and a glycerol such as glycerol, diglycerol and triglycerol; more preferably ethylene glycol, propylene glycol, 1,3-butanediol, dipropylene glycol, polyethylene glycol having a molecular weight of 1,000 or less, glycerol and diglycerol; and further preferably propylene glycol, 1,3-butanediol and glycerol; and still more preferably the polyol (d) comprises at least glycerol.

<6> The method for producing a coating film according to any of <1> to <5>, wherein the liquid oil (oil which is in a liquid state at 20° C.) is one or more selected from the group consisting of a hydrocarbon oil, a higher alcohol, a silicone oil and a fatty acid.

<7> The method for producing a coating film according to any of <1> to <6>, wherein a content of the component (d) in the composition Y is preferably 1% by mass or more and 40% by mass or less, more preferably 2% by mass or more and 25% by mass or less, further preferably 4% by mass or more and 20% by mass or less, and still more preferably 10% by mass or more and 20% by mass or less.

<8> The method for producing a coating film according to any of <1> to <7>, wherein a mass ratio of the component (d) to the component (c) (d/c) in the composition Y is preferably 1 or more and 30 or less, more preferably 1 or more and 25 or less, and further preferably 3 or more and 20 or less.

<9> The method for producing a coating film according to any of <1> to <8>, wherein the composition Y preferably comprises a polyol and a liquid oil and a mass ratio of the polyol to the liquid oil (polyol/liquid oil) is preferably 0.4 or more and 40 or less, more preferably 1 or more and 20 or less, and further preferably 2 or more and 10 or less.

<10> The method for producing a coating film according to any of <1> to <9>, wherein the composition Y further comprises a solid oil.

<11> The method for producing a coating film according to any of <1> to <9>, wherein the composition Y further comprises one or more solid oils selected from the group consisting of silicone wax, hydrocarbon wax, ester wax, a higher alcohol and ceramide.

<12> The method for producing a coating film according to <10> or <11>, wherein a content of the solid oil in the composition Y is preferably 0.1% by mass or more and 10% by mass or less, more preferably 0.5% by mass or more and 5% by mass or less, and further preferably 1% by mass or more and 3% by mass or less.

<13> The method for producing a coating film according to any of <1> to <12>, wherein the composition Y is an emulsion composition, preferably an oil-in-water emulsion composition or a water-in-oil emulsion composition, and more preferably a water-in-oil emulsion composition.

<14> The method for producing a coating film according to any of <1> to <13>, wherein the Step B) is a step of applying the composition Y to the skin by a unit other than electrostatic spraying.

<15> The method for producing a coating film according to any of <1> to <14>, further comprising a step of applying a cosmetic comprising a powder to the skin before, between or after the Step A) and the Step B).

<16> The method for producing a coating film according to any of <1> to <15>, wherein the coating film formed by electrostatic spraying in the Step A) is a porous coating film.
<17> The method for producing a coating film according to any of <1> to <16>, wherein the Step A) is a step of forming a coating film comprising a deposit of fiber by electrostatically spraying the composition X onto the skin by using an electrostatic spraying apparatus, and the electrostatic spraying apparatus comprises a container for storing the composition X, a nozzle for discharging the composition X, a unit for supplying the composition X stored in the container to the nozzle, and a power source for applying voltage to the nozzle.
<18> A composition Y comprising a component (c) and a component (d), the composition used for applying to skin by a unit other than electrostatic spraying to produce a coating film on the skin before or after the formation of the coating film on a surface of the skin by direct electrostatic spraying onto the skin:
(c) 0.5% by mass or more and less than 5% by mass of an adhesive polymer;
(d) one or more selected from the group consisting of a polyol and a liquid oil.
<19> The composition Y according to <18>, wherein the composition used for electrostatic spraying is a composition X comprising a component (a) and a component (b):
(a) one or more volatile substances selected from the group consisting of water, an alcohol and a ketone;
(b) a polymer capable of forming a coating film

EXAMPLES

Hereinafter the present invention will be described in detail with reference to Examples, but the scope of the present invention is not limited by these Examples. "%" means "% by mass" unless otherwise specified.

Synthetic Example 1 (Production of Poly(N-Propionylethyleneimine)-Modified Silicone)

19.0 g (0.12 mole) of diethyl sulfate and 81.0 g (0.82 mole) of 2-ethyl-2-oxazoline were dissolved in 203.0 g of dehydrated ethyl acetate, and the mixture was refluxed by heating in nitrogen atmosphere for 8 hours to synthesize terminal reactive poly(N-propionylethyleneimine). The number average molecular weight was determined by GPC to be 1,100. 300 g of a 33% ethyl acetate solution of side chain primary aminopropyl modified polydimethylsiloxane (weight average molecular weight 32,000, amine equivalent 2,000) was added thereto batchwise and the mixture was refluxed by heating for 10 hours. The reaction mixture was concentrated under reduced pressure to give an N-propionylethyleneimine-dimethylsiloxane copolymer in the form of a light yellow rubbery solid (390 g, yield 97%). The content of the organopolysiloxane segment in the final product was 75% by mass and the weight average molecular weight was 40,000. Neutralization titration with hydrochloric acid using methanol as a solvent has revealed that about 20% by mole of an amino group remains. This adhesive polymer had a maximum tensile shear load measured in accordance with JIS K 6850 of 8.6 N. The maximum tensile shear load of commercially available adhesive polymers was as described in Table 1.

| Name of raw material (Name of manufacturer) | Name of polymer | Maximum tensile shear load (N) |
|---|---|---|
| Kollidon 90F | Polyvinylpyrrolidone | 54.6 |
| Synthetic Example 1 | Poly(N-propionylethyleneimine)-modified silicone | 8.6 |
| Baycusan C2000 (COVESTRO AG) | Polyurethane-64 | 48.2 |
| PEG20000 | Polyethylene glycol (molecular weight 20,000) | 3.4 |
| Amphomer 28-4910 (AkzoNobel) | (Octylacrylamide/acrylate/butylaminoethyl methacrylate) copolymer | 20.5 |
| Amphomer LV-71 (AkzoNobel) | (Octylacrylamide/hydroxypropyl acrylate/butylaminoethyl methacrylate) copolymer | 32.3 |
| Amphomer HC (AkzoNobel) | (Alkyl acrylate·octyl acrylamide) copolymer | 9.7 |
| Resyn 28-2930 (AkzoNobel) | (VA/crotonic acid/vinyl neodecanoate) copolymer | 65.7 |
| Gantrez ES425 (Ashland) | (Vinyl methyl ether/butyl maleate) copolymer | 25.0 |
| Omnirez2000 (Ashland) | (Vinyl methyl ether/ethyl maleate) copolymer | 34.7 |
| Yodosol GH34F (AkzoNobel) | Alkyl acrylate copolymer ammonium | 40.5 |
| Yodoso IGH800F (AkzoNobel) | Alkyl acrylate copolymer ammonium | 27.3 |
| Diaformer Z651 (Mitsubishi Chemical Corporation) | (Acrylate/lauryl acrylate/stearyl acrylate/ethylamine oxide methacrylate) copolymer | 80.7 |
| Yukaformer 301 (Mitsubishi Chemical Corporation) | (Methacryloyloxyethylcarboxybetaine/alkyl methacrylate) copolymer | 34.0 |
| Yukaformer 104D (Mitsubishi Chemical Corporation) | (Methacryloyloxyethylcarboxybetaine/alkyl methacrylate) copolymer | 64.0 |
| Yukaformer 202 (Mitsubishi Chemical Corporation) | (Methacryloyloxyethylcarboxybetaine/alkyl methacrylate) copolymer | 79.6 |
| Yukaformer SM (Mitsubishi Chemical Corporation) | (Methacryloyloxyethylcarboxybetaine/alkyl methacrylate) copolymer | 57.4 |
| Yukaformer R205S (Mitsubishi Chemical Corporation) | (Methacryloyloxyethylcarboxybetaine/alkyl methacrylate) copolymer | 41.1 |

Test 1

Examples 1 to 14, Comparative Examples 1, 2

(1) Preparation of Composition for Spraying
  The compositions of Table 2 were used as a composition for spraying.
(2) Preparation of Composition Y
  The liquid formulations (composition Y) shown in Tables 3 to 5 were used.
(3) Process of Evaluation
  I. A commercially available skincare agent was applied to the skin.
  II. Electrostatic spraying was performed (Step A).
  An electrostatic spraying method was performed to one's cheek for 20 seconds using the electrostatic spraying apparatus 10 having the structure shown in FIG. 1 and the appearance shown in FIG. 2. The conditions of the electrostatic spraying method were as shown below.
    Voltage applied: 10 kV
    Distance between nozzle and skin: 100 mm
    Amount of discharge of composition for spraying: 5 mL/h
    Environment: 25° C., 30% RH
  A porous coating film made of a deposit of fiber was formed on the surface of the skin by the above electrostatic spraying. The coating film was in the form of a circle having a diameter of about 4 cm and a mass of about 5.5 mg. The thickness of the fiber measured by the above method was 506 nm.
  III. Composition Y was applied (Step B).
  IV. A commercially available concealer was applied.
  V. A commercially available powder foundation was applied.
  Then the coating film formed on the skin was subjected to sensory evaluation based on the following criteria. Five expert panelists evaluated the coating film for "no uncomfortable feeling immediately after application," "finished look 5 hours after application (coming off at edges)," "finished look 5 hours after application (crack at the center)," and "no feeling of float of powder 5 hours after application." Results are given by an integrated value of the five panelists.

[Evaluation]
(1) No uncomfortable feeling immediately after application
  5: Do not feel uncomfortable
  4: Hardly feel uncomfortable
  3: Feel a little uncomfortable
  2: Feel uncomfortable
  1: Feel very uncomfortable
(2) Finished look 5 hours after application (coming off at edges)
  5: No coming off of coating film observed
  4: Little coming off of coating film observed
  3: A little coming off of coating film observed
  2: Coming off of coating film observed
  1: Significant coming off of coating film observed
(3) Finished look 5 hours after application (crack at the center)
  5: No crack observed in coating film
  4: Little crack observed in coating film
  3: A little crack observed in coating film
  2: Crack observed in coating film
  1: Significant crack observed in coating film
(4) No feeling of float of powder 5 hours after application
  5: No feeling of float of powder
  4: Little feeling of float of powder
  3: A little feeling of float of powder
  2: Feeling of float of powder
  1: Significant feeling of float of powder

TABLE 2

| Component | Purity | Composition for spraying 1 | Composition for spraying 2 |
|---|---|---|---|
| (b) Polyvinylbutyral*1 | 100% | 15.00 | — |
| (b) Acrylates/octylacrylamide copolymer*2 | 100% | — | 30.00 |
| (a) Ethanol | 99.5% | 79.60 | 69.65 |
| Water | | 0.40 | 0.35 |
| Di(phytosteryl/octyl dodecyl) lauroyl glutamate*3 | 100% | 5.00 | — |
| Total | | 100.00 | 100.00 |

*1S-LEC B BM-1 (SEKISUI CHEMICAL CO.,LTD.)
*2DERMACRYL 79 (AkzoNobelSurfaceChemistryLLC)
*3ELDEW PS-203 (AJINOMOTO CO., INC.)

TABLE 3

| | | | Liquid formulation (milk) | | | | |
|---|---|---|---|---|---|---|---|
| | Component (% by mass) | | Example 1 Liquid formulation 1 | Example 2 Liquid formulation 2 | Example 3 Liquid formulation 3 | Example 4 Liquid formulation 4 | Example 5 Liquid formulation 5 |
| (c) | Synthetic Example 1 Solid content | | 1.20 | 0.80 | 2.00 | 1.20 | 1.20 |
| (d) | Glycerol | | 10.00 | 10.00 | 10.00 | 0.00 | 15.00 |
| Others | Dimethylpolysiloxane 50cs | | 2.00 | 2.00 | 2.00 | 2.00 | 2.00 |
| | Cetyl alcohol | | 0.34 | 0.34 | 0.34 | 0.34 | 0.34 |
| | Sphingolipid | | 1.00 | 1.00 | 1.00 | 1.00 | 1.00 |
| | Glyceryl behenate | | 0.34 | 0.34 | 0.34 | 0.34 | 0.34 |
| | Water | | 80.52 | 80.92 | 79.72 | 90.52 | 75.52 |
| | Polyoxyethylenesorbitan monostearate | | 0.20 | 0.20 | 0.20 | 0.20 | 0.20 |

TABLE 3-continued

| Liquid formulation (milk) | | | | | | |
|---|---|---|---|---|---|---|
| | Distearyldimonium chloride | 0.40 | 0.40 | 0.40 | 0.40 | 0.40 |
| | Methyl paraoxybenzoate | 0.20 | 0.20 | 0.20 | 0.20 | 0.20 |
| | Ethanol | 3.80 | 3.80 | 3.80 | 3.80 | 3.80 |
| | Total | 100.00 | 100.00 | 100.00 | 100.00 | 100.00 |
| | (c) | 1.20 | 0.80 | 2.00 | 1.20 | 1.20 |
| | (d) | 12.00 | 12.00 | 12.00 | 2.00 | 17.00 |
| | Water | 80.52 | 80.92 | 79.72 | 90.52 | 75.52 |
| | (d)/(c) | 10.00 | 15.00 | 6.00 | 1.67 | 14.17 |
| Evaluation | No uncomfortable feeling immediately after application | 21 | 22 | 20 | 21 | 21 |
| | Finished look 5 hours after application (coming off at edges) | 24 | 23 | 24 | 23 | 23 |
| | Finished look 5 hours after application (crack at center) | 23 | 21 | 24 | 24 | 23 |
| | No feeling of float of powder 5 hours after application | 23 | 23 | 22 | 20 | 23 |

| | Component (% by mass) | Example 6 Liquid formulation 6 | Example 7 Liquid formulation 7 | Example 8 Liquid formulation 8 | Comparative Example 1 Liquid formulation 9 | Comparative Example 2 Liquid formulation 10 |
|---|---|---|---|---|---|---|
| (c) | Synthetic Example 1 Solid content | 1.20 | 1.20 | 1.20 | 0.20 | 0.00 |
| (d) | Glycerol | 10.00 | 10.00 | 10.00 | 10.00 | 0.00 |
| | Dimethylpolysiloxane 50cs | 1.00 | 4.00 | 0.00 | 0.00 | 2.00 |
| Others | Cetyl alcohol | 0.34 | 0.34 | 0.00 | 0.00 | 0.34 |
| | Sphingolipid | 1.00 | 1.00 | 0.00 | 0.00 | 1.00 |
| | Glyceryl behenate | 0.34 | 0.34 | 0.34 | 0.34 | 0.34 |
| | Water | 81.52 | 78.52 | 83.86 | 84.86 | 91.72 |
| | Polyoxyethylenesorbitan monostearate | 0.20 | 0.20 | 0.20 | 0.20 | 0.20 |
| | Distearyldimonium chloride | 0.40 | 0.40 | 0.40 | 0.40 | 0.40 |
| | Methyl paraoxybenzoate | 0.20 | 0.20 | 0.20 | 0.20 | 0.20 |
| | Ethanol | 3.80 | 3.80 | 3.80 | 3.80 | 3.80 |
| | Total | 100.00 | 100.00 | 100.00 | 100.00 | 100.00 |
| | (c) | 1.20 | 1.20 | 1.20 | 0.20 | — |
| | (d) | 11.00 | 14.00 | 10.00 | 10.00 | 2.00 |
| | Water | 81.52 | 78.52 | 83.86 | 84.86 | 91.72 |
| | (d)/(c) | 9.17 | 11.67 | 8.33 | 50.00 | — |
| Evaluation | No uncomfortable feeling immediately after application | 21 | 21 | 21 | 23 | 24 |
| | Finished look 5 hours after application (coming off at edges) | 23 | 23 | 22 | 16 | 15 |
| | Finished look 5 hours after application (crack at center) | 23 | 22 | 21 | 14 | 15 |
| | No feeling of float of powder 5 hours after application | 23 | 23 | 22 | 22 | 17 |

TABLE 4

| Composition for spraying + liquid formulation (milk) | | |
|---|---|---|
| | | Example 9 |
| I | Composition for spraying | Composition for spraying 2 |
| II | Composition Y | Liquid formulation 1 |
| Evaluation | No uncomfortable feeling immediately after application | 20 |
| | Finished look 5 hours after application (coming off at edges) | 22 |
| | Finished look 5 hours after application (crack at center) | 21 |
| | No feeling of float of powder 5 hours after application | 23 |

TABLE 5

| Liquid formulation (milk) | | | |
|---|---|---|---|
| | Component (% by mass) | Liquid formulation 11 | Liquid formulation 12 |
| (c) | Synthetic Example 1 Solid content | | 0.60 |
| | Polyvinyl alcohol*4 | 1.20 | 0.30 |
| | Polyvinylpyrrolidone*5 | | 0.30 |
| (d) | Glycerol | 10.00 | 7.00 |
| | 1,3-propanediol | | 3.00 |
| | Dimethylpolysiloxane 50 cs | 2.00 | 1.00 |
| | Isononyl isononanoate | | 0.50 |
| | Octyldodecanol | | 0.50 |
| Others | Cetyl alcohol | 0.34 | 0.30 |
| | Microcrystalline wax | | 0.04 |
| | Sphingolipid | 1.00 | 1.00 |
| | Glyceryl behenate | 0.34 | 0.34 |
| | Water | 80.52 | 80.52 |
| | Polyoxyethylenesorbitan monostearate (20 E.O.) | 0.20 | 0.20 |

TABLE 5-continued

|   |   |   |   |
|---|---|---|---|
|   | Distearyldimonium chloride | 0.40 | 0.40 |
|   | Methyl paraoxybenzoate | 0.20 | 0.20 |
|   | Ethanol | 3.80 | 3.80 |
| Total |   | 100.00 | 100.00 |
| (c) |   | 1.20 | 1.20 |
| (d) |   | 12.00 | 12.00 |
| Water |   | 80.52 | 80.52 |
| (d)/(c) |   | 10.00 | 10.00 |

Composition for spraying + liquid formulation (milk)

|   |   | Example 10 | Example 11 |
|---|---|---|---|
| I | Composition for spraying | Composition for spraying 1 | Composition for spraying 1 |
| II | Composition Y | Liquid formulation 11 | Liquid formulation 12 |
| Evaluation | No uncomfortable feeling immediately after application | 20 | 20 |
|   | Finished look 5 hours after application (coming off at edges) | 22 | 23 |
|   | Finished look 5 hours after application (crack at center) | 22 | 22 |
|   | No feeling of float of powder 5 hours after application | 23 | 22 |

*4GOHSENOL EG-40 (The Nippon Synthetic Chemical Industry Co., Ltd.)
*5PVP K-90 (Tokyo Chemical Industry Co., Ltd.)

TABLE 6

Liquid formulation (milk)

|   | Component (% by mass) | Liquid formulation 13 |
|---|---|---|
| (c) | Synthetic Example 1 Solid content | 0.90 |
|   | Polyvinyl alcohol*4 | 0.30 |
| (d) | Glycerol | 7.00 |
|   | 1,3-propanediol | 3.00 |
|   | Dimethylpolysiloxane 50 cs | 1.00 |
|   | Isononyl isononanoate | 0.25 |
|   | Sunflower oil | 0.25 |
|   | Octyldodecanol | 0.50 |
| Others | Cetyl alcohol | 0.30 |
|   | Microcrystalline wax | 0.04 |
|   | Sphingolipid | 1.00 |
|   | Glyceryl behenate | 0.34 |
|   | Water | 80.52 |
|   | Polyoxyethylenesorbitan monostearate (20 E.O.) | 0.20 |
|   | Distearyldimonium chloride | 0.40 |
|   | Methyl paraoxybenzoate | 0.20 |
|   | Ethanol | 3.80 |
|   | Total | 100.00 |
| (c) |   | 1.20 |
| (d) |   | 12.00 |
| Water |   | 80.52 |
| (d)/(c) |   | 10.00 |

Composition for spraying + liquid formulation (milk)

|   |   | Example 12 |
|---|---|---|
| I | Composition for spraying | Composition for spraying 1 |
| II | Composition Y | Liquid formulation 12 |
| Evaluation | No uncomfortable feeling immediately after application | 20 |
|   | Finished look 5 hours after application (coming off at edges) | 22 |
|   | Finished look 5 hours after application (crack at center) | 22 |
|   | No feeling of float of powder 5 hours after application | 21 |

Test 2

The following steps were performed using the compositions shown in Table 7 and Table 8. The resulting products were evaluated in the same manner as in Test 1.

I. A commercially available skin care agent was applied to the skin.
II. Electrostatic spraying was performed (Step A).
III. Composition Y was applied (Step B).
IV. A commercially available concealer was applied.
V. Electrostatic spraying was performed (Step A).
VI. Composition Y was applied.
VII. A commercially available powder foundation was applied.

TABLE 7

|   |   |   | Example 13 |
|---|---|---|---|
|   |   | Skin care preparation | Toner |
| I |   | Composition for spraying | Composition for spraying 1 |
| II |   | Composition Y | Liquid formulation 1 |
|   |   | Concealer | Concealer |
| I |   | Composition for spraying | Composition for spraying 1 |
| II |   | Composition Y | Liquid formulation 1 |
|   |   | Foundation | Powder foundation |
| Evaluation |   | No uncomfortable feeling immediately after application | 20 |
|   |   | Finished look 5 hours after application (coming off at edges) | 24 |
|   |   | Finished look 5 hours after application (crack at center) | 23 |
|   |   | No feeling of float of powder 5 hours after application | 24 |

TABLE 8

|   |   |   | Example 14 |
|---|---|---|---|
|   |   | Skin care preparation | Toner |
| II |   | Composition Y | Liquid formulation 1 |
| I |   | Composition for spraying | Composition for spraying 1 |
|   |   | Concealer | Concealer |
| I |   | Composition for spraying | Composition for spraying 1 |
| II |   | Composition Y | Liquid formulation 10 |
|   |   | Foundation | Powder foundation |
| Evaluation |   | No uncomfortable feeling immediately after application | 20 |
|   |   | Finished look 5 hours after application (coming off at edges) | 23 |
|   |   | Finished look 5 hours after application (crack at center) | 22 |
|   |   | No feeling of float of powder 5 hours after application | 24 |

REFERENCE SIGNS LIST

10 Electrostatic spraying apparatus
11 Low-voltage power source
12 High-voltage power source
13 Auxiliary electronic circuit
14 Pump mechanism
15 Container
16 Nozzle
17 Pipe
18 Flexible Pipe
19 Current limiting resistor
20 Housing

The invention claimed is:

1. A method for producing a coating film on a skin, comprising:
   A) electrostatically spraying a composition X comprising a component (a) and a component (b) directly to the skin to form a porous coating film comprising a deposit of continuous fiber on a surface of the skin:
      (a) 55% by mass or more and 96% by mass or less of one or more volatile substances selected from the group consisting of water, an alcohol and a ketone;
      (b) 4% by mass or more and 45% by mass or less of a polymer capable of forming a coating film; and
   B) applying a composition Y other than the composition X comprising a component (c) and a component (d) to the skin by a unit other than electrostatic spraying, wherein a mass ratio of the component (d) to the component (c) (d/c) in the composition Y is 1 or more and 30 or less,
   in the order presented or in reverse order:
      (c) 0.5% by mass or more and less than 5% by mass of an adhesive polymer selected from the group consisting of an adhesive rubber polymer, an adhesive silicone polymer, an adhesive acrylic polymer, an adhesive urethane polymer and a nonionic polymer and having a maximum tensile shear load measured in accordance with JIS K 6850 of 1 N or more and 90 N or less;
      (d) one or more selected from the group consisting of a polyol and a liquid oil.

2. The method for producing a coating film according to claim 1, wherein a mass ratio of the component (d) to the component (c) (d/c) in the composition Y is 1 or more and 25 or less.

3. The method for producing a coating film according to claim 1, wherein a content of the component (d) in the composition Y is 1% by mass or more and 40% by mass or less.

4. The method for producing a coating film according to claim 1, wherein the composition Y further comprises a solid oil.

5. The method for producing a coating film according to claim 1, wherein the composition Y comprises the polyol and the liquid oil.

6. The method for producing a coating film according to claim 1, wherein the composition Y is a water-in-oil emulsion composition.

7. The method for producing a coating film according to claim 1, wherein the A) forms a coating film comprising a deposit of fiber by electrostatically spraying the composition X to the skin by using an electrostatic spraying apparatus, and the electrostatic spraying apparatus comprises a container for storing the composition X, a nozzle for discharging the composition X, a unit for supplying the composition X stored in the container to the nozzle, and a power source for applying voltage to the nozzle.

* * * * *